US005804445A

United States Patent [19]
Brasier

[11] Patent Number: 5,804,445
[45] Date of Patent: Sep. 8, 1998

[54] HIGH AFFINITY MUTANTS OF NUCLEAR FACTOR-INTERLEUKIN 6 AND METHODS OF USE THEREFOR

[75] Inventor: Allan R. Brasier, Galveston, Tex.

[73] Assignee: Board of Regents, The University of Texas System, Austin, Tex.

[21] Appl. No.: 585,197

[22] Filed: Jan. 11, 1996

[51] Int. Cl.$^6$ .......................... C07K 14/435; C12N 1/20; C12N 15/85

[52] U.S. Cl. .......................... 435/375; 435/243; 435/325; 530/324

[58] Field of Search ................................ 530/324; 514/2, 514/44; 435/375, 325, 243; 424/93.2

[56] References Cited

FOREIGN PATENT DOCUMENTS 0 273 085   7/1988   European Pat. Off. .

OTHER PUBLICATIONS

Tijan R. "Molecular machines that control genes." Scientific American, pp. 55–61, Feb. 1995.
Agre et al., "Cognate DNA Binding Specificity Retained After Leucine Zipper Exchange Between GCN4 and C/EBP," *Science*, 246:922–926, 1989.
Akira et al., "A Nuclear Factorfor IL–6 Expression (NF–IL6) is a member of a C/EBP Family," *EMBO J.*, 9:1897–1906, 1990.
Baichwal and Sugden, "Vectors for Gene Transfer Derived from Animal DNA Viruses: Transient and Stable Expression of Transferred Genes," In: Gene Transfer, Kucherlapati R., ed., New York: Plenum Press, pp. 117–148, 1986.
Bangham et al., *J. Mol. Biol.*, 13:238–52, 1965.
Blatter et al., "Identification of an Amino Acid–Base Contact in the GCN4–DNA Complex by Bromouracil–Mediated Photocrosslinking," *Nature*, 359:650–652, 1992.
Brasier et al., "A Family of Constitutive C/EBP–like DNA Binding Proteins Attenuate the IL–1 Alpha Induced, NF Kappa B Mediated Trans–Activation of the Angiotensinogen Gene Acute–Phase Response Element," *EMBO J.*, 9:3933–3944, 1990.
Brasier and Kumar, "Identification of a Novel Determinant for Basic Domain–Leucine Zipper (bZIP) DNA–Binding Activity in the Acute–Phase Inducible Nuclear Factor–Interleukin 6 Transcription Factor," *J. Biol. Chem.*, 269:10341–10351, 1994.
Cao et al., "Regulated Expression of three C/EBP Isoforms During Adipose Conversion of 3T3–L1 Cells," *Genes Dev.*, 5:1538–1552, 1991.
Chang et al., Molecular Cloning of a Transcription Factor, "AGP/EBP, that Belongs to Members of the C/EBP Family," *Mol. Cell Biol.*, 10:6642–6653, 1990.
Cuenoud and Schepartz, "Design of a Metallo–bZIP Protein that Discriminates Between CRS and AP1 Target Sites: Selection Against AP1," *Proc. Nat'l Acad. Sci. U.S.A.*, 90:1154–1159, 1993.
Curiel, "Gene Transfer to Respiratory Epithelial Cells via Receptor Mediated Endocytosis," *Am J. Resp. Cell and Mol. Biol*, 6:247, 1995.
Deamer and Uster, "Liposome Preparation: Methods and Mechanisms," *Liposomes*, M. Ostro, ed., 1983.
Descombes et al., "LAP, a Novel Member of the C/EBP Gene Family Encodes a Liver–Enriched Transcriptional Activator Protein," *Genes and Development*, 4:1541–1551, 1990.
Descombes and Schibler, "A Liver–Enriched Transcriptional Activator Protein, LAP, and a Transcriptional Inhibitory Protein, LIP, are translated from the same mRNA," *Cell*, 67:569–579, 1991.
Ellenberger et al., "The GCN4 Basic Region Leucine Zipper Binds DNA as a Dimer of Uninterrupted Alpha–Helices: Crystal Structure of the Protein–DNA Complex," *Cell*, 71:1223–1237, 1992.
Ferkol et al., *FASEB J.*, 7:1081–1091, 1993.
Gomez–Foix et al., "Adenovirus–Mediated Transfer of the Muscle Glycogen Phosphorylase Gene Into Hepatocytes Confers Altered Regulation of Glycogen," *J. Biol. Chem.*, 267:25129–25134, 1992.
Graham and Prevec, "Manipulation of Adenovirus Vector," In: Methods in Molecular Biology: Gene Transfer and Expression Protocol, E.J. Murray (ed.), Clifton, NJ:Humana Press, 7:109–128, 1991.
Gregoriadis, *Drug Carriers in Biology and Medicine*, G. Gregoriadis, ed., pp. 287–341, 1979.
Grunhaus and Horowitz, "Adenovirus as Clonging Vector," *Seminar in Virology*, 3:237–252, 1992.
Johnson, "Identification of C/EBP Basic Region Residues Involved in DNA Sequence Recognition and Hals–Site Spacing Preference," *Mol. Cell Biol.*, 13:6919–6930, 1993.
Kaneda et al., "Increased Expression of DNA cointroduced with Nuclear Protein in Adult Rat Liver," *Science*, 243:375–378, 1989.
Kato et al., "Expression of Hepatitis B Virus Surface Antigen in Adult Rat Liver," *J. Biol. Chem.*, 266:3361–3364, 1991.
Kouzarides and Ziff, "The role of the Leucine Zipper in the Fos–jun Interaction," *Nature*, 336–646–651, 1988.
Krylov et al., "A Thermodynamic Scale for Leucine Zipper Stability and Dimerization Specificity: E and G Interhelical Interactions," *EMBO J.*, 13:2849–2861, 1994.
Landschulz et al., The Leucine Zipper: A Hypothetical Structure Common to a New Class of DNA–Binding Proteins, *Science*, 240:1759, 1988.
Landschulz et al., "The DNA Binding Domain of the Rat Liver Nuclear Protein C/EBP is Bipartite," *Science*, 243:1681–1688, 1989.

(List continued on next page.)

Primary Examiner—Douglas W. Robinson
Assistant Examiner—Amy J. Nelson
Attorney, Agent, or Firm—Arnold, White & Durkee

[57] ABSTRACT

The present invention relates to inhibitors of the sequence specific transcription factor nuclear factor IL-6 (NF-IL6) and methods of use therefor. In particular, substitution mutants in the N-terminus of the NF-IL6 tryptic core domain are disclosed that have a higher binding affinity for the DNA binding site than does the wild-type sequence.

21 Claims, 13 Drawing Sheets

OTHER PUBLICATIONS

Levrero et al., "Defective and Nondefective Adenovirus Vectors for Expressing Foreign Genes In Vitro and In Vivo," *Gene*, 101:195–202, 1991.

Nicolas and Rubenstein, "Retroviral Vectors," In: Vectors: A Survey of Molecular Cloning Vectors and Their Uses, Rodriguez and Denhardt (eds.), Stoneham: Butterworth, pp. 493–513, 1988.

O'Shea et al., "X–Ray Structure of the GCN4 Leucine Zipper, a Two–Stranded, Parallel Coiled Coil," *Science*, 254:539–544, 1991.

Poli et al., "IL–6DBP, A Nuclear Protein Involved in Interleukin–6 Signal Transduction, Defines A New Family of Leucine Zipper Proteins Related to C/EBP," *Cell*, 63:643–653, 1990.

Pu and Struhl, "The Leucine Zipper Symmetrically Positions the Adjacent Basic Region for Specific DNA Binding," *Proc. Nat'l Acad. Sci. U.S.A.*, 88:6901–6905, 1991.

Rich et al., "Developoment and Analysis of Recombinant Adenoviruses for Gene Therapy of Cystic Fibrosis," *Hum. Gene Ther.*, 4:461–476, 1993.

Ridgeway, "Mammalian Expression Vectors," In: Vectors: A Survey of Molecular Cloning Vectors and Their Uses, Rodriguez and Denhardt (eds.), Stoneham: Butterworth, pp. 467–492, 1988.

Stratford–Perricaudet and Perricaudet, "Gene Transfer Into Animals: The Promise of Adenovirus," pp. 51–61, In: Human Gene Transfer, O. Cohen–Haguenauer and M. Boiron (eds.), Editions John Libbey Eurotext, France, 1991.

Szoka and Papahadjopoulos, *Proc. Nat'l Acad. Sci. U.S.A.*, 75:4194–98, 1978.

Temin, "Retrovirus Vectors for Gene Transfer: Efficient Integration Into and Expression of Exogenous DNA in Vertebrate Cell Genome," In: Gene Transfer, Kucherlapati (ed.), New York: Plenum Press, pp. 149–188, 1986.

Vinson et al., "Dimerization Specificity of the Leucine Zipper–Containing bZIP Motif on DNA Binding: Prediction and Rational Design," *Genes Devel.*, 7:1047–1058, 1993.

Wagner et al., *Science*, 260:1510–1513, 1990.

Wang et al., "Delivery of Antisense Oligodeoxyribonucleotides Against the Human EGF Receptor Into Cultured KBV Cells with Liposomes Conjugated to Folate via Polyethylene Glycol," *Proc. Nat'l Acad Sci. U.S.A.*, 92:3318–3322, 1995.

Williams et al., "A Family of C/EBP–Related Proteins Capable of Forming Covalently Linked Leucine Zipper Dimers In Vitro," *Genes Devel.*, 5:1553–1567, 1991.

Wong et al., "Appearance of β–Lactamase Activity in Animal Cells Upon Liposome Mediated Gene Transfer," *Gene*, 87–94, 1980.

Wu and Wu, *Adv. Drug Delivery Rev.*, 12:159–167, 1993.

```
M   A266 V   D   K   H   S   D272 E   Y   K   I   R   R   E
ATG GCC GTG GAC AAG CAC AGC GAC GAG TAC AAG ATC CGG CGC GAG
            CSSD

R   N   N   I   A   V   R   K   S   R   D   K   V   K   M
CGC AAC AAC ATC GCC GTG CGC AAG AGC CGC GAC AAG GTC AAG ATG
        DNA-CONTACT

R   N   L   E   T   Q   H   K   V   L   E   L   T   A   E
CGC AAC CTG GAG ACG CAG CAC AAG GTC CTG GAG CTC ACG GCC GAG
                                            LEUCINE ZIPPER

N   E   R   L   Q   K   K   V   E   Q   L   S   R   E   L
AAC GAG CGG CTG CAG AAG AAG GTC GAG CAG CTG TCG CGC GAG CTC

S   T   L   R   N   L   F   K   Q   L   P   E   P   L   L
AGC ACC CTG CGG AAC TTG TTC AAG CAG CTG CCC GAG CCC CTG CTC

A   S   S   G   H   C
GCC TCC TCC GGC CAC TGC TAG
```

FIG. 1

|  | M | A266 | V267 | D268 | K269 | H270 | S271 | D272 | E | Y | TCDWT |
|---|---|---|---|---|---|---|---|---|---|---|---|
|  | ATG | GCC | GTG | GAC | AAG | CAC | AGC | GAC | GAG | TAC | |
|  | M | A | A | D | K | H | S | D | E | Y | V267A |
|  | ATG | GCC | GCC | GAC | AAG | CAC | AGC | GAC | GAG | TAC | |
|  | M | A | V | A | K | H | S | D | E | Y | D268A |
|  | ATC | GCC | GTG | GCC | AAG | CAC | AGC | GAC | GAG | TAC | |
|  | M | A | V | D | A | H | S | D | E | Y | K269A |
|  | ATG | GCC | GTG | GAC | GCC | CAC | AGC | GAC | GAG | TAC | |
|  | M | A | V | D | K | A | S | D | E | Y | H270A |
|  | ATG | GCC | GTG | GAC | AAG | GCC | AGC | GAC | GAG | TAC | |
|  | M | A | V | D | K | H | A | D | E | Y | S271A |
|  | ATG | GCC | GTG | GAC | AAG | CAC | GCC | GAC | GAG | TAC | |
|  | M | A | V | D | K | H | S | A | E | Y | D272A |
|  | ATG | GCC | GTG | GAC | AAG | CAC | AGC | GCC | GAG | TAC | |

FIG. 3

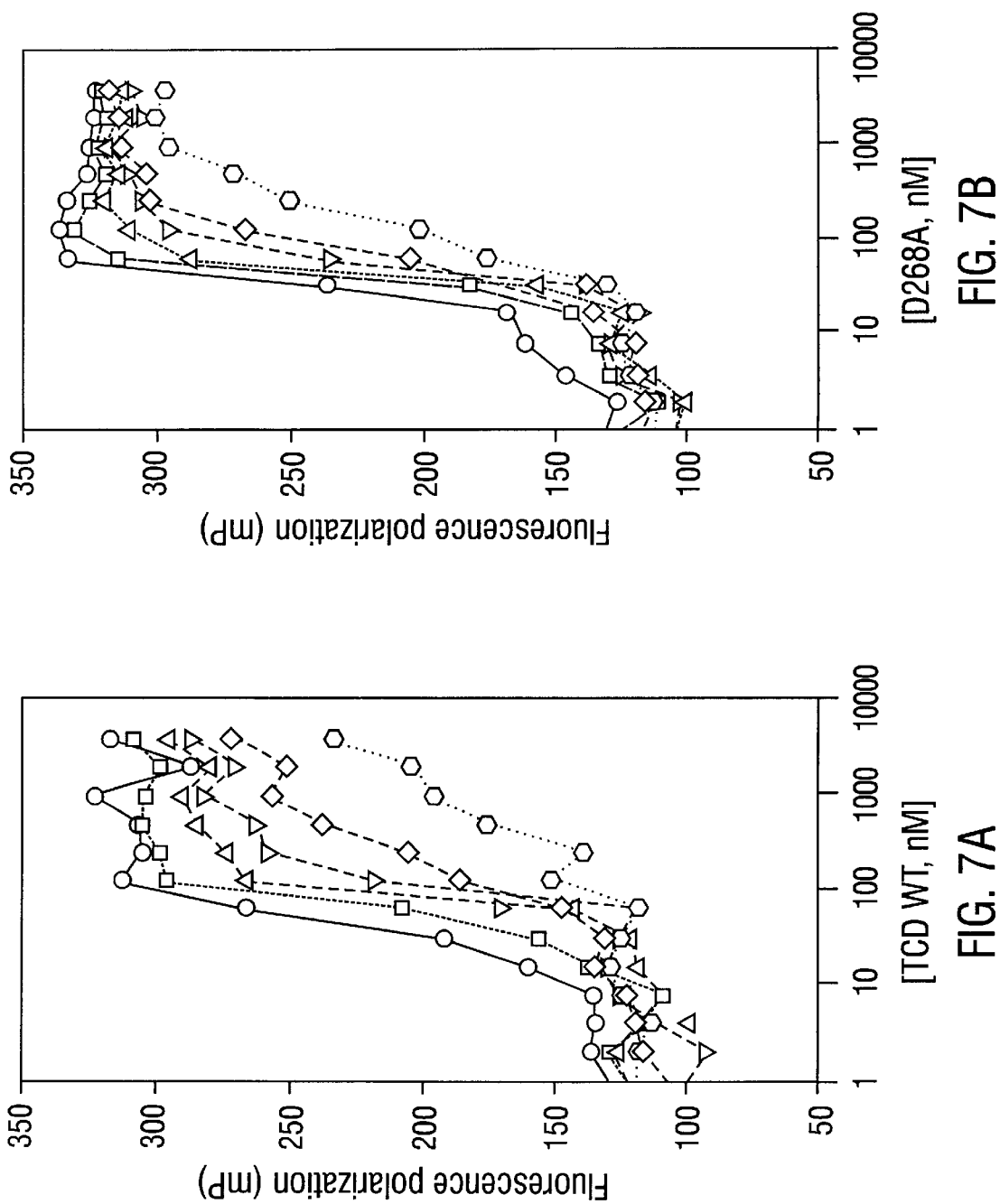

5,804,445

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 87 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Val  Lys  Ser  Lys  Ala  Lys  Lys  Thr  Val  Asp  Lys  His  Ser  Asp  Glu  Tyr
 1              5                        10                       15
Lys  Ile  Arg  Arg  Glu  Arg  Asn  Asn  Ile  Ala  Val  Arg  Lys  Ser  Arg  Asp
              20                        25                       30
Lys  Val  Lys  Met  Arg  Asn  Leu  Glu  Thr  Gln  His  Lys  Val  Leu  Glu  Leu
             35                    40                        45
Thr  Ala  Glu  Asn  Glu  Arg  Leu  Gln  Lys  Lys  Val  Glu  Gln  Leu  Ser  Arg
        50                   55                        60
Glu  Leu  Ser  Thr  Leu  Arg  Asn  Leu  Phe  Lys  Gln  Leu  Pro  Glu  Pro  Leu
 65                      70                        75                       80
Leu  Ala  Ser  Ser  Gly  His  Cys
                      85
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS:

(D) TOPOLOGY: linear (xi) SEQUENCE DESCRIPTION: SEQ ID NO:2:

Ala Val Asp Lys His Ser Asp
1               5

(2) INFORMATION FOR SEQ ID NO:3:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (xi) SEQUENCE DESCRIPTION: SEQ ID NO:3:

GATCCACCAC AGTTGGGATT TCCCAACCTG ACCA                         34

(2) INFORMATION FOR SEQ ID NO:4:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (xi) SEQUENCE DESCRIPTION: SEQ ID NO:4:

GTGGTGTCAA CCCTAAAGGG TTGGACTGGT CTAG                         34

(2) INFORMATION FOR SEQ ID NO:5:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (xi) SEQUENCE DESCRIPTION: SEQ ID NO:5:

GATCCACCAC AGTTGTGATT TCACAACCTG ACCA                         34

(2) INFORMATION FOR SEQ ID NO:6:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (xi) SEQUENCE DESCRIPTION: SEQ ID NO:6:

GTGGTGTCAA CACTAAAGTG TTGGACTGGT CTAG                         34

(2) INFORMATION FOR SEQ ID NO:7:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (xi) SEQUENCE DESCRIPTION: SEQ ID NO:7:

GATCCGGACG TCACTTGCAC AATCTTAATA A                            31

(2) INFORMATION FOR SEQ ID NO:8:

(i) SEQUENCE CHARACTERISTICS:
  (A) LENGTH: 31 base pairs
  (B) TYPE: nucleic acid
  (C) STRANDEDNESS: single
  (D) TOPOLOGY: linear ( x i ) SEQUENCE DESCRIPTION: SEQ ID NO:8:

GCCTGCAGTG AACGTGTTAG AATTATTCTA G                                31

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GATCCACCAC AGTTGTGATT TCACAACCTG ACCA                             34

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTGGTGTCAA CACTAAAGTG TTGGACTGGT CTAG                             34

( 2 ) INFORMATION FOR SEQ ID NO:11:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GATCCACCAC ATGTTGGATT TCCGATACTG ACCA                             34

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTGGTGTACA ACCTAAAGGC TATGACTGGT CTAG                             34

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AGGATTACCA TGGCCGTGGA CAAGCACAGC GACGAG                           36

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGGATTACCA TGGCCGTGGC CAAGCACAGC GACGAG 36

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:15:

AGGATTACCA TGGCCGTGGC CAAGCACAGC GACGAG 36

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:16:

AGGATTACCA TGGCCGTGCA CGCCCACAGC GACGAG 36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

AGGATTACCA TGGCCGTGGA CAAGGCCAGC GACGAG 36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

AGGATTACCA TGGCCGTGGA CAAGCACGCC GACGAG 36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

AGGATTACCA TGGCCGTGGA CAAGCACAGC GCCGAG 36

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:20:

AAGGCGGGGG GATCCTAGCA GTGGCCGGAG GAGGCGAGC 39

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:21:

Met Ala Val Asp Lys His Ser Asp Glu Tyr
1               5                   10

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ATGGCCGTGG ACAAGCACAG CGACGAGTAC        30

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:23:

Met Ala Ala Asp Lys His Ser Asp Glu Tyr
1               5                   10

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

ATGGCCGTGG CCAAGCACAG CGACGAGTAC        30

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:25:

Met Ala Val Ala Lys His Ser Asp Glu Tyr
1               5                   10

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

ATGGCCGTGG CCAAGCACAG CGACGAGTAC 30

( 2 ) INFORMATION FOR SEQ ID NO:27:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:27:

Met Ala Val Asp Ala His Ser Asp Glu Tyr
1               5                   10

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

ATGGCCGTGC ACGCCCACAG CGACGAGTAC 30

( 2 ) INFORMATION FOR SEQ ID NO:29:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:29:

Met Ala Val Asp Lys Ala Ser Asp Glu Tyr
1               5                   10

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

ATGGCCGTGG ACAAGGCCAG CGACGAGTAC 30

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:31:

Met Ala Val Asp Lys His Ala Asp Glu Tyr
1               5                   10

( 2 ) INFORMATION FOR SEQ ID NO:32:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ATGGCCGTGG ACAAGCACGC CGACGAGTAC 30

(2) INFORMATION FOR SEQ ID NO:33:

(i) SEQUENCE CHARACTERISTICS:
(A) LENGTH: 10 amino acids
(B) TYPE: amino acid
(C) STRANDEDNESS:
(D) TOPOLOGY: linear (xi) SEQUENCE DESCRIPTION: SEQ ID NO:33:

Met Ala Val Asp Lys His Ser Ala Glu Tyr
1               5                   10

(2) INFORMATION FOR SEQ ID NO:34:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:34:

ATGGCCGTGG ACAAGCACAG CGCCGAGTAC 30

(2) INFORMATION FOR SEQ ID NO:35:

(i) SEQUENCE CHARACTERISTICS:
(A) LENGTH: 81 amino acids
(B) TYPE: amino acid
(C) STRANDEDNESS:
(D) TOPOLOGY: linear (xi) SEQUENCE DESCRIPTION: SEQ ID NO:35:

Met Ala Val Asp Lys His Ser Asp Glu Tyr Lys Ile Arg Arg Glu Arg
1               5                   10                  15

Asn Asn Ile Ala Val Arg Lys Ser Arg Asp Lys Val Lys Met Arg Asn
            20                  25                  30

Leu Glu Thr Gln His Lys Val Leu Glu Leu Thr Ala Glu Asn Glu Arg
        35                  40                  45

Leu Gln Lys Lys Val Glu Gln Leu Ser Arg Glu Leu Ser Thr Leu Arg
    50                  55                  60

Asn Leu Phe Lys Gln Leu Pro Glu Pro Leu Leu Ala Ser Ser Gly His
65                  70                  75                  80

Cys (2) INFORMATION FOR SEQ ID NO:36:

(i) SEQUENCE CHARACTERISTICS:
(A) LENGTH: 246 base pairs
(B) TYPE: nucleic acid
(C) STRANDEDNESS: single
(D) TOPOLOGY: linear (xi) SEQUENCE DESCRIPTION: SEQ ID NO:36:

ATGGCCGTGG ACAAGCACAG CGACGAGTAC AAGATCCGGC GCGAGCGCAA CAACATCGCC 60
GTGCGCAAGA GCCGCGACAA GGTCAAGATG CGCAACCTGG AGACGCAGCA CAAGGTCCTG 120
GAGCTCACGG CCGAGAACGA GCGGCTGCAG AAGAAGGTCG AGCAGCTGTC GCGCGAGCTC 180
AGCACCCTGC GGAACTTGTT CAAGCAGCTG CCCGAGCCCC TGCTCGCCTC CTCCGGCCAC 240
TGCTAG 246

HIGH AFFINITY MUTANTS OF NUCLEAR FACTOR-INTERLEUKIN 6 AND METHODS OF USE THEREFOR

The government may own rights in this invention pursuant to funding from the National Institutes of Health, grant no. 1 R29 HL45500-05.

BACKGROUND OF THE INVENTION

I. Field of the Invention

The present invention relates generally to inhibitors of nuclear factor-interleukin-6 (NF-IL6) and methods of use therefor. More particularly, the invention provides high binding affinity variants of the tryptic core domain of NF-IL6, pharmaceutical compositions thereof and therapeutic applications in the treatment of cytokine-related pro-inflammatory reactions.

II. Related Art

Asthma is the most prevalent chronic illness in childhood. While clinical management of reactive airway disease has improved over the last decade, asthma nevertheless is a leading cause of morbidity in childhood. Asthma is etiologically linked to viral infection in early childhood, and one of the major infectious agents responsible is Respiratory Syncytial Virus (RSV). One of the primary events in RSV-induced asthma is the direct release of pro-inflammatory cytokines by infected airway epithelium initiating an inflammatory cascade resulting in edema and bronchoconstriction. These pro-inflammatory cytokines, interleukin-6 (IL6), interleukin-8 (IL8) and GM-CSF are part of a cytokine network regulated by the shared transcription factor nuclear factor-IL6 (NF-IL6).

NF-IL6 is a C/EBP family member first identified in the regulation of hepatic acute-phase reactants (Brasier et al., 1990; Poli et al., 1990) and cytokine gene promoters (Akira et al., 1990). As a consequence of systemic injury or inflammation, NF-IL6 is synthesized in the mammalian hepatocyte where it binds to distinct cis-regulatory elements in the promoters of acute-phase reactants and regulates their activity. The effect of NF-IL6 on transcription appears to be dependent on the promoter context in which it binds.

Although NF-IL6 activates the cytokine IL6 gene promoter (Akira et al. 1990), work also as demonstrated that NF-IL6 attenuates activity of the inducible enhancer of the angiotensinogen gene, termed the acute-phase response element, by displacing the potent NF-KB transactivator from an overlapping binding site (Brasier et al., 1990a).

In a previous study (Brasier and Kumar, 1994), the inventors demonstrated a tryptic core domain (TCD) of NF-IL6, spanning residues 266-345, produced by controlled protease digestion of a complex of DNA and NF-IL6. Included in this region was the leucine zipper domain (residues 303-345) that constitutes the DNA binding domain of the polypeptide. Of this region, the N-terminal portion (266-272) was identified as being involved in complex stabilization.

Because of the role played by NF-IL6 in stimulating cytokine production, the action of this molecule presents a potential point for clinical intervention in the development of a cytokine-driven inflammatory response. Therefore, there is a need for effective inhibitors of NF-IL6 function. There remains a lack of basic understanding regarding the way this molecule interacts with target sequences, however, and no suitable inhibitors have yet been developed.

SUMMARY OF THE INVENTION

Therefore, it is an object of the present invention to provide inhibitors of NF-IL6. In addition, it is an object of the present invention to provide methods for the use of such inhibitors in reducing or blocking the action of NF-IL6.

In fulfilling these objects, there is provided a polypeptide comprising an NF-IL6 tryptic core domain, wherein the N-terminus of said core domain has a net charge that is less negative than the N-terminus of wild-type NF-IL6 tryptic core domain. In another embodiment, the tryptic core domain corresponds to residues 266 to 345 of wild-type NF-IL6 tryptic core domain. In yet another embodiment, the N-terminus corresponds to residues 266 to 272 of wild-type NF-IL6 tryptic core domain. In still yet another embodiment, the N-terminus is at least one unit charge less negatively charged than wild-type NF-IL6 tryptic core domain. A specific example of this is provided where the N-terminus lacks one of the aspartic acid residues found in the wild-type NF-IL6 tryptic core domain and has substituted therefore an uncharged or positively charged residue. Another example is where the N-terminus lacks both aspartic acid residues found in the wild-type NF-IL6 tryptic core domain and has substituted therefore at least one uncharged or positively charged residue. The substitutions may be alanine, glycine or threonine residue.

Also provided is a pharmaceutical composition comprising (i) a polypeptide comprising an NF-IL6 tryptic core domain, wherein the N-terminus of said core domain has a net charge that is less negative than wild-type NF-IL6 tryptic core domain; and (ii) a pharmaceutically acceptable excipient, diluent or carrier. In a particular embodiment, the pharmaceutical composition is formulated with folate-conjugated bovine serum albumin or with a liposome.

Another aspect of the present invention is a method for inhibiting NF-IL6 function in a cell comprising the steps of (i) providing a polypeptide comprising an NF-IL6 tryptic core domain, wherein the N-terminus of said core domain has a net charge that is less negative than wild-type NF-IL6 tryptic core domain; and (ii) contacting said cell with said polypeptide. Again, one particular embodiment includes formulation with a liposome.

Still another aspect of the present invention involves a method for treating pro-inflammatory cytokine production in a patient comprising the steps of (i) providing pharmaceutical composition comprising (a) a polypeptide comprising an NF-IL6 tryptic core domain, wherein the N-terminus of said core domain has a net charge that is less negative than wild-type NF-IL6 tryptic core domain and (b) a pharmaceutically acceptable excipient, diluent or carrier; and (ii) administering said polypeptide to said patient. Administration may comprise inhalation or an enema. The polypeptide may be formulated with folate-conjugated bovine serum albumin or with a liposome.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 2A: Raw data and curve-fitting of fluorescence polarization titration for TCD WT:F-APRE M6 DNA binding. Static measurements were taken after blanking the polarimeter against a cuvette containing binding the buffer alone. The raw data was plotted (solid line) as a function of the TCD WT concentration (nM). In this assay, the value for fluorescence polarization of the probe alone is 65 mP. The signal to noise ratio, the total light intensity of the probe relative to buffer alone is 90:1. The sigmoidal curve was then fitted to several models of single DNA binding; the simplest model that fit the data best was of a single site binding reaction (Equation 1, Methods). Nonlinear least squares regression analysis was used to fit the raw data to the relationship $f(x)+AX+BC)/(X+C)$, where A represents the maximum polarization values, B represents the minimum polarization values, respectively (mP). C represents the equilibrium disassociation constant (Kd, nM) using the Levenberg-Marquart algorithm using constraints as described in the Examples. FIG. 2B: Hill plot of Log(Bound/Free) versus Log(Free) from fluorescence polarization curve. The data are represented by a straight line Log (Bound/Free)+0.59+0.9Log(F) ($R_2$=0.99). FIG. 2C: Percent residuals (difference between raw data and curve fit in percentages) are plotted on the same X-axis scale as for the raw data. The two curves are closely approximated at the TCD WT peptide concentrations that determine the Kd. FIG. 2D: Scatchard plot of Bound/Free versus Bound for the same binding reaction. Least squares linear regression analysis is shown in the solid line described by the equation (Bound/Free)+0.69–0.15(Bound) (R2=0.97). Using this curve to estimate the Kd gives the value of 6.7 nM, in close agreement with the estimates from the Hill plot and Sigmoidal curve fitting algorithms.

FIG. 3—SEQUENCE OF ALANINE SUBSTITUTION MUTANTS IN THE CSSD OF THE TCD. Systematic replacement of native amino acids for alanine residues was accomplished by designing PCR primers with the alanine codon (GCC) replacing native amino acids at $V^{267}$ to $D^{272}$. All peptides were expressed at similar levels in E. coli BL21 (DE3)pLysS and were prepared homogeneously as for the TCD WT peptide. All peptides lack the initiator methionine as does the TCD WT. The CSSD mutations are referred to by the convention TCD X-NNN-A, where X is the single letter amino acid code for the native amino acid substituted, NNN corresponds to the location of the amino acid relative to the translation initiation site, and A is the alanine substitution.

FIG. 6D shows Log ($K_{obs}$) vs. Log [NaCl] as a function of pH. Each set of binding isotherms was deconvoluted and $K_{obs}$ estimated. The binding data can be approximated by a straight line for pH 5.0 Log ($K_{obs}$)=8.35+ 0.218 Log [NaCl].

FIGS. 7A–7C—TCDD268A AND D272A BIND F-APRE M6 WITH HIGHER AFFINITY IN THE PRESENCE OF NaCl. Fluorescence polarization was measured to quantitate TCD WT, D268A and D272A binding to F-APRE M6 using 0.5 nM F-APRE M6 in simultaneous assays in sodium chloride for (●) 16 mM, (■) 25 mM, (▲) 40 mM, (▼) 63 mM, and (octagon) 158 mM at 23° C. Log ($K_{obs}$) was plotted as a function of Log[NaCl]. Binding isotherms from titrations in FIG. 7A, FIG. 7B and FIG. 7C were deconvoluted to determine Kobs (Methods) for each salt concentration.

DETAILED DESCRIPTION OF THE INVENTION

Figure 2A:
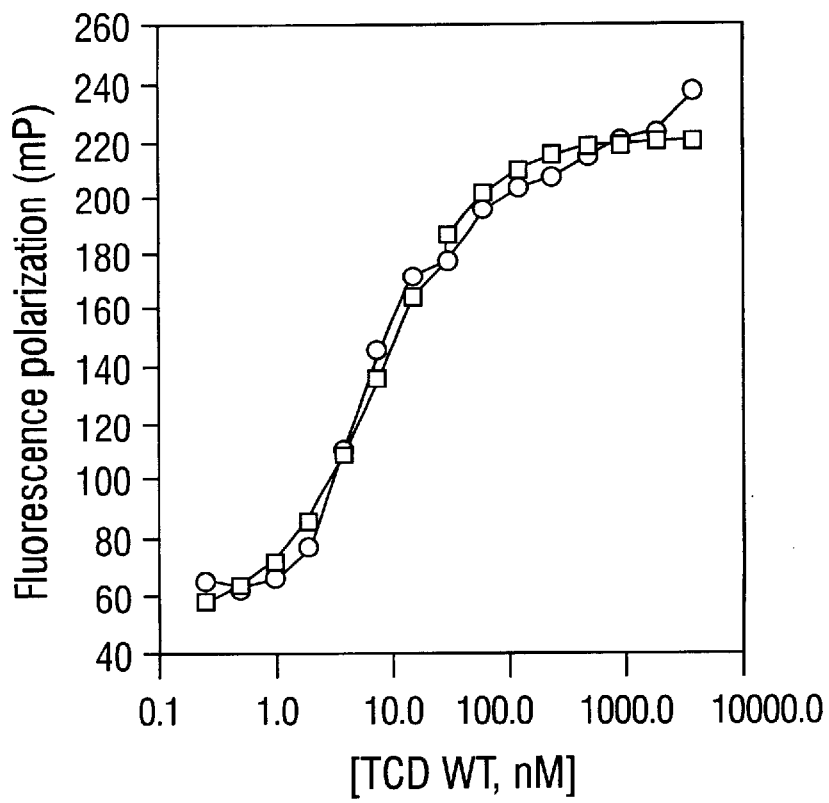
FIGS. 2A–2D—Deconvolution of Fluorescence Polarization Titration Curves for TCD WT Binding to F-APRE M6.
Figure 2B:
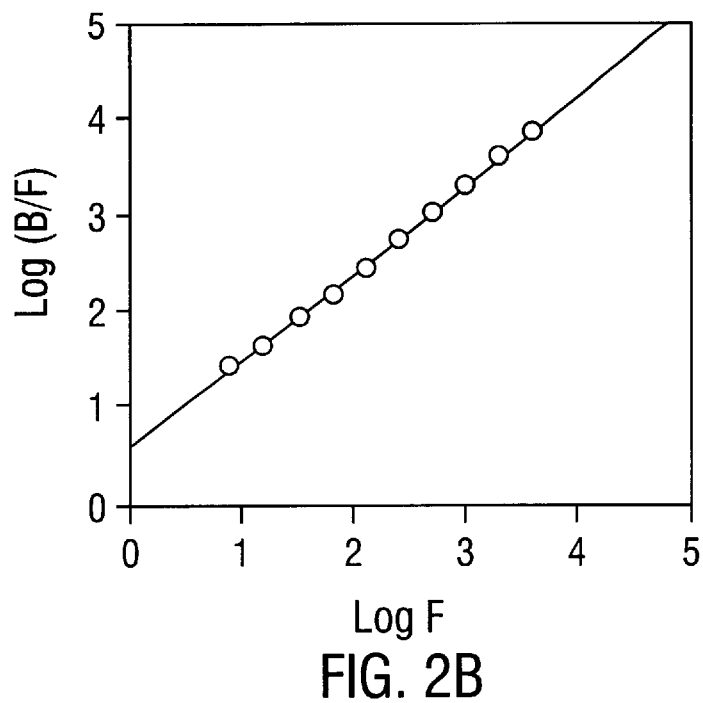
Figure 2C:
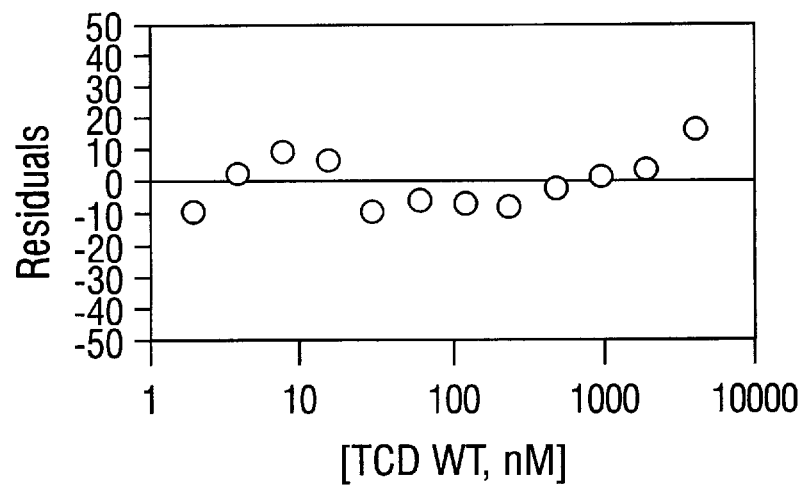
Figure 2D:
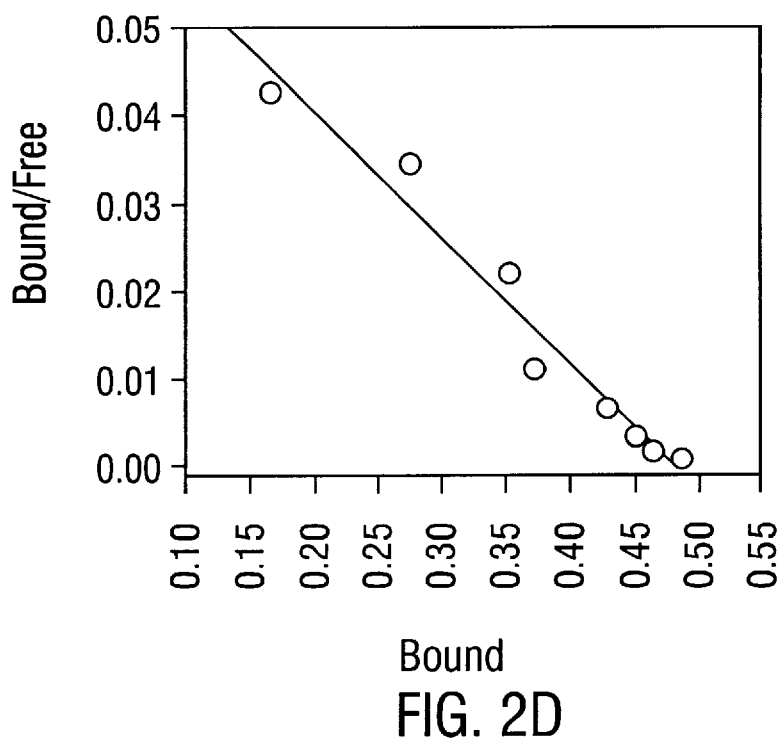

Leucine zippers are amphipathic coiled-coil dimerization domains (Landschulz et al., 1988b; Kouzarides and Ziff, 1988; O'Shea et al., 1991; Vinson et al., 1993; Ellenberger et al., 1992) found in certain DNA-binding polypeptides. Detailed structural analysis of recombinant C/EBPα DNA binding peptides has helped define the basic domain-leucine zipper (bZIP) motif. The bZIP motif contains two functionally distinct elements. At the $NH_2$ terminus is a region rich in the basic amino acids, and at the COOH terminus is a repeat of 3–4 hydrophobic leucine residues (Landschulz et al., 1988, 1989; Kouzarides and Ziff, 1988).

Multiple lines of evidence indicate that the basic region of the bZIP protein motif is involved in DNA contact, including mutational analysis (Landschulz et al., 1989) and "domain swapping" studies in which the basic region of C/EBP is replaced with the homologous region of the yeast bZIP protein GCN4 (Agre et al., 1989, Johnson, 1993). Moreover, bromodeoxyuracil cross-linking studies using GCN4 bZIP peptides identify atomic interactions between thymidine and a highly conserved asparaginase residue (Asn235) within the basic domain (Blatter et al., 1992). Finally, the crystal structure of the GCN4-DNA complex demonstrates interaction of basic domain amino acid side chains through hydrogen bonds to the DNA phosphodiester backbone and with bases in the major groove of the GCN4 binding site (Ellenberger et al., 1992).

Precise orientation and spacing between the basic region and leucine zipper is necessary for DNA binding. The only tolerated amino acid substitutions between these two motifs are those that produce an integral number of α-helical turns (Pu and Struhl, 1991). Moreover, alterations in the angle at which the two basic domains are fixed in space alters DNA binding specificity (Cuenoud and Schepartz, 1993). These data argue that the leucine zipper also participates in DNA binding by correctly positioning the two basic regions for contact with adjacent half-site DNA.

NF-IL6 represents the human homolog of rat liver-enriched transcriptional activator protein (Descombes et al., 1990), interleukin-6-response element DNA-binding protein (Poli et al., 1990), α1-acid glycoprotein enhancer binding protein (Chang et al., 1990), mouse C/EBPβ (Cao et al., 1991), or C/EBP-related protein 2 (Williams et al., 1991) and, like its rodent counterparts, contains three in-frame initiator methionine residues producing NH2-terminal-deleted proteins of about 38, 33 and 16 kDa in size (Descombes et al., 1990, Descombes and Schibler, 1991).

Comparison of the predicted amino acid sequence of the 16 kDa COOH terminus of NF-IL6 with other proteins in the National Biomedical Research Foundation data base identified an 84 amino acid region homologous to the DNA-binding domain of C/EBPα (Akira et al., 1990). Selective expression in E. coli of the 16 kDa COOH terminus, termed LIP for liver-enriched inhibitory protein, produces a DNA binding peptide that binds to identical sequences as the mature 33 kDa protein (Descombes and Schibler, 1991). These data indicate that the 16 kDa COOH terminus of liver-enriched transcriptional activator protein contains the DNA-binding domain.

As mentioned above, a tryptic core domain from the COOH terminal region of NF-IL6, referred to as TCD, has been identified in protease protection assays. The present invention involves the identification of high affinity inhibitors of NF-IL6 derived from the NH$_2$ terminal region of the TCD, previously identified as contributing to the stabilization of NF-IL6 leucine zipper binding. These inhibitors may be used to alleviate the effects of certain conditions involving pro-inflammatory cytokine production.

A. Definitions

Negatively-Charged Amino Acid—Negatively charged amino acids are Aspartic Acid and Glutamic Acid.

Positively-Charged Amino Acid—Positively charged amino acids are Lysine, Arginine and Histidine.

Uncharged Amino Acid—An uncharged amino acid is defined to include both non-polar and polar uncharged amino acids. These include Alanine, Valine, Leucine, Isoleucine, Proline, Methionine, Phenylalanine, Tryptophan, Cysteine, Glycine, Serine, Threonine, Tyrosine, Asparagine and Glutamine.

Tryptic Core Domain (TCD)—TCD is a functionally defined region in COOH terminus of NF-IL6. The function of interest is protease resistance in the presence of bound target nucleic acid. In one embodiment, this region includes residues 266-345 of wild-type NF-IL6, as shown in SEQ ID NO. 1. EMBL Accession No. X52560; Akira et al. (1990). Depending on the target sequence employed, reaction conditions and allelic variation in NF-IL6, however, the region may vary slightly.

Complex Stabilizing Subdomain (CSSD)—CSSD is a functionally defined region in the NH$_2$ terminus of TCD. The function of interest is the ability to stabilize the interaction of the TCD with a target nucleic acid sequence. In one embodiment, this region includes residues 266-272 of wild-type NF-IL6, as shown in SEQ ID NO. 1. Depending on the target sequence employed, reaction conditions and allelic and species variation in NF-IL6, however, the region may vary slightly.

Pro-Inflammatory Cytokine Production—Proinflammatory cytokines are peptide hormones that initiate and maintain local or systemic inflammation. Examples of proinflammatory cytokines include, but are not limited to) interleukin-1 (IL-1), tumor necrosis factor (TNF), granulocyte macrophage-colony stimulating factor (GM-CSF), IL-8 and IL-6. These cytokines are produced by injured airway epithelium and their function is important to the pathogenesis of pneumonia and infectious asthma. Local or systemic bacterial or viral infections, the acute phase response, tumor induced cachexia, and acute gastroenteritis are all conditions that are associated with the elaboration of proinflammatory cytokines.

Target Sequence—The general consensus sequence that loosely fits an NF-IL6 target is a redundant series of the sequence 5'-TT/GNNGNAAT/G-3'. Particular sequences that can be employed in various embodiments are described below.

B. NF-IL6 Inhibitors

Previously, the minimum boundaries of the basic amino acid-rich domain of NF-IL6 were defined (Brasier and Kumar, 1994). Using a T7 promoter/polymerase expression system, high levels of the recombinant COOH domain of NF-IL6 were produced. Probing of the DNA-binding domain by controlled endoprotease digestion identified a trypsin-resistant core domain (TCD), located at residues 266-345. This region includes the bZIP domain (303-345) and a second region involved in complex stabilization, located between residues 266 and 272. This region is characterized by the presence of two negatively-charged (underlined) and two positively-charged (bold) amino acids and has the wild-type sequence:

A V D̲ K H S D̲ (SEQ ID NO:2)

It now appears that this region not only stabilizes the bZIP-target sequence binding, but actually interacts with some portion of the target sequence itself. This fact was determined by measuring the binding affinity of peptide variants in which negatively charged residues in the CSSD were substituted with more positively charged amino acids. This observation runs counter to predictions derived from previous crystallographic studies on GCN4 (Ellenberger et al., 1992), which indicated that the amino terminus of the GCN4 peptide did not interact with the target.

Thus, in accordance with the present invention, peptides that have greater binding affinity for the NF-IL6 target sequence are prepared by manipulating the CSSD region such the net positive charge of this seven amino acid stretch is increased. Because of the increased positive charge, interaction with the negatively charged target nucleic acid is enhanced, resulting in higher affinity binding than even the wild-type sequence. With a greater binding affinity than wild-type, the peptides can "outbind" and, hence, inhibit the action of wild-type NF-IL6. The carboxy-terminal end of the CSSD may be extended to position 275 (Lys).

As defined herein, a decrease in the net negative charge can be accomplished by substituting at least one residue in the wild-type sequence with an amino acid having a more positive charge, i.e., a change of one "unit charge" in the positive direction from the wild-type sequence. Thus, either of the negatively charged aspartic acid residues can be substituted with an uncharged or positively charged amino acid, any of the uncharged residues (Ala, Val and Ser) may be substituted with a positively charged amino acid (Lys, Arg and His) and the positively charged residues may only be substituted with another positively charged amino acid, at least for single point mutants.

In one embodiment, a single residue is altered in the 266 to 272 region. Alternatively, two, three, four, five, six or even seven residues may be altered at the same time while following the above-described scheme. It is important to note that it has been demonstrated that even a single unit charge change in the positive direction can result in inhibitory action, i.e., the ability to outbind the wild-type sequence. While all of the potential sequence variants may not show improved binding to target sequences when compared to the wild-type sequence, it is a simple matter to determine, in binding assays, whether a given variant shows such improved binding.

For example, a comparison of equilibrium disassociation constants of peptides is a suitable estimate of binding affinity. This comparison may be made on the basis of gel mobility shift assays followed by saturation or Scatchard plot analysis of the results. The following are detailed protocols for the application of such assays to the present invention.

Electrophoretic gel mobility shift assays are performed with the double-stranded target oligonucleotide radioactively labeled with [$\alpha$-$^{32}$P]dATP by Klenow DNA polymerase to a specific activity of $10^6$ cpm/pmol. Twenty-thousand cpm are used in each binding reaction constituting 10 fmol of DNA probe in a total volume of 20 $\mu$l. Scatchard analysis is performed using increasing amounts of probe with 50 ng of purified peptide. Binding volume is increased to 48 $\mu$l and contained in 1 mg/ml BSA as a nonspecific carrier. Bound and free DNA complexes are advantageously separated and quantitated by exposure of the gel to a phosphorimager screen.

"Off-rate" determinations may be made on the basis of nitrocellulose binding assays. Nitrocellulose filter binding assays are performed using homogeneous fractions of wild-type and variant peptides. Peptide is added to a known concentration of target nucleic acid in a 50 $\mu$l final volume of binding buffer containing 10 mM Tris-HCl (pH 7.4), 50 mM KCl, 1 mM DTT, 0.1 mM EDTA. The off-rate ($K_{off}$) is determined by using $4\times10^{-10}$M binding activity and $8\times10^{-10}$M probe in the same binding buffer. Samples are allowed to bind for 20 min until equilibrium was reached and then a 1000-fold excess of oligonucleotide is added as a trap for disassociated protein. At selected times, samples are filtered, washed and quantitated.

As defined above, target sequences for NF-IL6 can only loosely fit a consensus sequence. Examples of suitable target sequences are:

APRE WT: GATCCACCACAGTTGGGATTTC-CCAACCTGACCA (SEQ ID NO:3)
GTGGTGTCAACCCTAAAGGGTTGGACTG-GTCTAG (SEQ ID NO:4)
APRE M6: GATCCACCACAGTTGTGATTTCA-CAACCTGACCA (SEQ ID NO:5)
GTGGTGTCAACA<u>C</u>TAAAG<u>T</u>GTTGGACTGGTCTAG (SEQ ID NO:6)
NF-IL6WT: GATCCGGACGTCACTTGCACAATCT-TAATAA (SEQ ID NO:7)
GCCTGCAGTGAACGTGTTAGAATTATTCTAG (SEQ ID NO:8)

Other suitable target sequences can be constructed by those of skill in the art based on the consensus sequence, as well as by mutagenizing any of the wild-type sequences, followed by screening for binding to wild-type NF-IL6 or one of its nucleic acid-binding fragments.

While the inhibitory peptides have, to this point, been defined in terms of the CSSD, it also is important to define the remainder of the molecule that constitutes an inhibitor. While the CSSD plays an important role in stabilizing the interaction of the bZIP domain, it also is necessary that the bZIP domain be available to bind the target sequence competitively with the wild-type NF-IL6 molecule. The bZIP region extends from approximately amino acid 275 (glutamic acid) to 345 (cysteine) of the wild-type NF IL-6 molecule. This region contains two functionally distinct domains that have properties essential for DNA-binding, and thus essential for the inhibitory functions of the NF-IL6 antagonist molecules. The basic region, represented by amino acids 273 to 303, is important for DNA contact and influences binding, specifically for the DNA target. The leucine zipper region, contained in amino acids 303-345, is necessary for dimerization, i.e., to hold two molecules together (an obligate requirement for DNA binding), and plays a role in correct positioning (orientation and spacing) of the basic region for binding with the appropriate target DNA.

Having thus defined the minimal elements of an inhibitor peptide, it also should be noted that the inhibitor must not contain all of the wild-type amino acids NH$_2$-terminal to the CSSD. Rather, by deletion, substitution or insertion, those domains outside CSSD must differ from the wild-type domain such that (i) there is no induction of transcription but (ii) binding of the inhibitor to the target sequence still occurs. At least four domains important for transcriptional activation have been identified, one around amino acid 235 (threonine), and three others in the NH$_2$-terminus (amino acids 24-33, 62-82 and 90-100) of the molecule.

In a preferred embodiment, the inhibitors comprise variants of the tryptic core domain, designated as NFBDs. The tryptic core domain is an 8.8 kD fragment derived from the NF-IL6 16 kD molecule. This peptide is protected from proteolysis by its interaction with the target sequence. However, sequences extending to and including amino acid 199 at the NH$_2$-terminus may be included in the inhibitor. NFBDs contain one or two alanines substituted for the aspartic acid residues of the CSSD. The coding sequence for the tryptic core domain is cloned into an expression vector and mutagenized using site-directed methodology.

C. Expression Constructs Encoding NF-IL6 Inhibitory Peptides

The inhibitory peptides according to the present invention may be provided via expression constructs that carry nucleic acids encoding the inhibitory peptides. Throughout this application, the term "expression construct" is meant to include any type of genetic construct containing a nucleic acid coding for a gene product in which part or all of the nucleic acid sequence is capable of being transcribed. Typical expression vectors include bacterial plasmids or phage, such as any of the pUC or Bluescript™ plasmid series or, as discussed further below, viral vectors.

In preferred embodiments, the nucleic acid encodes an NF-IL6 inhibitory peptide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the peptide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter. An example of a tissue specific promoter that would be useful in accordance with the present invention is the fatty acid binding protein promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an NF-IL6-inhibitory peptide following transfection can be optimized. For example, selection of a promoter which is active specifically in lung cells, such as tyrosinase (melanoma) will permit lung-specific expression of the inhibitory peptide. Further, selection of a promoter that is regulated in response to specific physiologic signals can permit inducible expression of an inhibitory protein. For example, a nucleic acid under control of the human PAI-1 promoter results in expression inducible by tumor necrosis factor. Tables 1 and 2 list several elements/promoters which may be employed, in the context of the present invention, to regulate the expression of NFBDs. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding an NF-IL6 inhibitory peptide in an expression construct (Table 1 and Table 2). Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II $5_\alpha^k$ |
| MNC Class II HLA-DRα |
| β-Actin |
| Muscle Creatine Kinase |
| Prealbumin (Transthyretin) |
| Elastase I |

TABLE 1-continued

ENHANCER

Metallothionein
Collagenase
Albumin Gene
α-Fetoprotein
τ-Globin
β-Globin
c-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 2

| Element | Inducer |
| --- | --- |
| MT II | Phorol Ester (TPA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorobol Ester (TPA) |
| Stromelysin | Phorbol Ester (TPA), IL-1 |
| SV40 | Phorobol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester (TPA) |
| Tumor Necrosis Factor | PHA |
| Tyroid Stimulating Hormone α Gene | Thyroid Hormone |

In certain embodiments of the invention, the delivery of a nucleic acid in a cell may be identified in vitro or in vivo by including a marker in the expression construct. The marker would result in an identifiable change to the transfected cell permitting easy identification of expression. Usually, the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed simultaneously with the nucleic acid encoding an NFBD. Further examples of selectable markers are well known to one of skill in the art.

One also may include a polyadenylation signal to effect proper polyadenylation of the transcript. The nature of the polyadenylation signal is not believed to be crucial to the successful practice of the invention, and any such sequence may be employed. The inventors have employed the SV40 polyadenylation signal in that it was convenient and known to function well in the target cells employed. Also contemplated as an element of the expression cassette is a terminator. These elements can serve to enhance message levels and to minimize read through from the cassette into other sequences.

In certain embodiments of the invention, the expression construct advantageously comprises a virus or engineered construct derived from a viral genome. The ability of certain viruses to enter cells via receptor-mediated endocytosis, to integrate into the host cell genome and to express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. Also, they can accommodate only up to 8 kilobases of foreign genetic material, but can be readily introduced in a variety of cell lines and laboratory animals (Nicolas and Rubenstein, 1988; Temin, 1986).

(i) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol and env that code for capsid proteins, polymerase enzyme and envelope components, respectively. A sequence found upstream from the gag gene, termed ψ, functions as a signal for packaging of the genome into virions. Two long terminal repeat (LTR) sequences are present at the 5' and 3' ends of the viral genome. These contain strong promoter and enhancer sequences and also are required for integration into the host cell genome (Coffin, 1990).

In order to construct a retroviral vector, a nucleic acid encoding an NF-IL6 is inserted into the viral genome in the place of certain viral sequences to produce a virus that is replication-defective. In order to produce virions, a packaging cell line containing the gag, pol, and env genes but without the LTR and ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

(ii) Adenovirus

Knowledge of the genetic organization of adenovirus, a 36 kB, linear and double-stranded DNA virus, allows substitution of a large piece of adenoviral DNA with foreign sequences up to 7 kB (Grunhaus and Horwitz, 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the nucleic acid encoding the inhibitory peptide at the position from which the E1 coding sequences have been removed. However, the position of insertion of the NFBD coding region within the adenovirus sequences is not critical to the present invention. The nucleic acid encoding a inhibitory peptide transcription unit also may be inserted in lieu of the deleted E3 region in E3 replacement vectors as described previously by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1992), muscle injection (Ragot et al., 1993), peripheral intravenous injection (Herz and Gerard, 1993), and stereotactic inoculation into the brain (Le Gal La Salle et al., 1993).

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedman, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

D. Methods for Gene Transfer

In order to effect expression of nucleic acid constructs, the expression vector carrying the constructs must be delivered into a cell. As described above, the one mechanism for delivery is via viral infection where the expression vector is encapsidated in an infectious adenovirus particle. For non-infectious vectors, other means may be required.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

In one embodiment of the invention, the adenoviral expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an NF-IL6 inhibitory peptide also may be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a K-ras antisense construct may be delivered via this method.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085). Another receptor ligand combination that may advantageously be employed according to the present invention is the folate-folate receptor system. Lee and Low (1994); Wang et al. (1995). Other examples include surfactant protein A-polylysine conjugates for delivery to airway cells (Ross, 1995), receptor-mediated endocytosis to respiratory epithelial cells (Curiel, 1995) and use of the polymeric immunoglobulin receptor for gene transfer into airway epithelium (Ferkol, 1995).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery of expression construct in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. During ex vivo culture, the expression vector can express the antisense K-ras construct. Finally, the cells may be reintroduced into the original animal, or administered into a distinct animal, in a pharmaceutically acceptable form by any of the means described below.

E. Pharmaceutical Compositions

Where clinical application of NF-IL6 inhibitors or expression vectors coding therefore is undertaken, it will be necessary to prepare the complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the inhibitory peptide or expression vector encoding the inhibitory peptide, dissolved or dispersed in a pharmaceutically acceptable carrier or aqueous medium. Such compositions also are referred to as inocula. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

As mentioned above, a preferred form for delivery of an expression vector according to the present invention is via liposomes. Liposomes also may be used to deliver formulated peptides. "Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY–YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al., J. Mol. Biol. 13:238–52 (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated peptide is removed by centrifugation at 29,000×g and the liposomal pellets washed. The washed liposomes are resuspended at an appropriate total phospholipid concentration, e.g., about 50–200 mM. The amount of peptide encapsulated can be determined in accordance with the method of Lowry. After determination of the amount of peptide encapsulated in the liposome preparation, the liposomes may be diluted to about 100 micrograms of antigen per 0.5 ml and stored at 4° C. until use.

F. Doses and Routes of Administration

The inhibitory peptides and expression vectors of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic agent is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic peptide included in a unit dose will range from about 10 $\mu$g to 10 mg, from about 100 $\mu$g to 5 mg, and from about 1–2 mg.

G. Clinical Conditions Susceptible to Treatment With NF-IL6 Inhibitory Peptides A variety of different conditions may be treated according to the present invention. For example, postinfectious asthma is such a candidate disease. RSV and other viruses, including influenza, and respiratory infections caused by other agents, such as mycoplasma, can initiate airway inflammation that results in bronchoconstriction and asthma. The phenomenon of cytokine production by airway epithelial cells can result in this airway hyper-reactivity. Inhaled NF-IL6 antagonists should prevent postinfectious asthma.

Bacterial infections of the GI tract, including Salmonella and Shigella, produce disease by invading the gut epithelial cell lining. The gut epithelial cells, like infected airway epithelial cells, synthesize and release proinflammatory cytokines to produce local and systemic inflammation. Local inflammation in the gut results in fluid loss (diarrhea) with subsequent dehydration and is a major cause of mortality in third world countries. Chronic inflammatory bowel disease, an idiopathic inflammatory condition called ulcerative colitis or Crohn's disease, is the consequence of local gut inflammation. In the appropriate setting, oral or rectally-administered NF-IL6 antagonists should prevent the gut inflammation and its associated clinical manifestations.

Cutaneous or pulmonary burns stimulate the local production of cytokines that result in edema, pain and inflammation associated with thermal injuries or UV light-induced injuries. Topical or inhalational administration of NF-IL6 antagonists will be useful for the treatment of these conditions. Patients with particular types of cancers produce cytokines that result in wasting and a chronic acute phase reaction. Intravenous administration of NF-IL6 should be useful for the treatment of these conditions. Gout, rheumatoid arthritis and septic arthritis produce local joint inflammation through the elaboration of cytokines by fibroblasts and macrophages that line the synovial space. These cytokines stimulate the production of collagenases that destroy the cartilage and joint space. Intrarticular injections of NF-IL6 antagonists may block the production of cytokines; this would have beneficial effects in preserving joint function in arthritis.

H. EXAMPLES

Example 1

MATERIALS AND METHODS (a) Oligonucleotides

Double-stranded oligodeoxynucleotides were synthesized using standard phosphoramidite chemistry; the deprotected DNA-strands were annealed at 1:1 molar ratios, determined spectrophotometrically assuming a molar extinction coefficient of $E_{260}$=20 μg/ml/cm. The sequences are presented below, corresponding to nucleotides -557 to -528 of the rat angiotensinogen promoter with BamHI/BglII compatible ends. Underlining shows changes from the wild-type sequence:

5'-GATCCACCACAGTTGTGATTTCACAACCTGACCA-3' (SEQ ID NO: 9) APRE M6
GTGGTGTCAAC<u>A</u>CTAAAG<u>T</u>GTTGGACTGGTCTAG (SEQ ID NO: 10)
5'-GATCCACCACATGTTGGATTTCCGATACTGACCA-3' (SEQ ID NO: 11) APRE M2
GTGGTGTA<u>CA</u>ACCTAAAGG<u>CT</u>A<u>T</u>GACTGGTCTAG (SEQ ID NO: 12)

Fluorescein-labeled DNA was produced by incorporating the phosphoramidite Fluorescein-$C_6$-dG into the first position of the antisense (bottom) strand of APRE M6 during the oligonucleotide synthesis. A six-carbon spacer limits effects of fluorescein on DNA-binding and the rotational freedom of the fluorescein molecule. The efficiency of fluorescein incorporation exceeds 99%. F-APRE M6 was then annealed to the unlabeled antisense strand as described.

(b) Construction of Alanine substituted NF-IL6 CSSD expression vectors

The expression vector for the NF-IL6 tryptic core domain peptides was constructed by ligating NcoI-BamHI restriction fragments containing the appropriate coding sequences into the NcoI-BamHI-digested T7 promoter/polymerase expression plasmid pET3d. Studier et al. (1990). These coding sequences were generated by polymerase chain reaction using the following upstream primer oligonucleotides:

5'-AGG ATT ACC ATG GCC GTG GAC AAG CAC AGC GAC GAG-3' for TCDWT (SEQ ID NO: 13);
5'-AGG ATT ACC ATG GCC GTG <u>GTG</u> GCC AAG CAC AGC GAC GAG-3' for V267A (SEQ ID NO: 14);
5'-AGG ATT ACC ATG GCC GTG <u>GCC</u> AAG CAC AGC GAC GAG-3' for D268A (SEQ ID NO: 15);
5'-AGG ATT ACC ATG GCC GTG CAC <u>GCC</u> CAC AGC GAC GAG-3' for K269A (SEQ ID NO: 16);
5'-AGG ATT ACC ATG GCC GTG GAC AAG <u>GCC</u> AGC GAC GAG-3' for H270A (SEQ ID NO: 17);
5'-AGG ATT ACC ATG GCC GTG GAC AAG CAC <u>GCC</u> GAC GAG-3' for S271A (SEQ ID NO: 18);
5'-AGG ATT ACC ATG GCC GTG GAC AAG CAC AGC <u>GCC</u> GAG-3' for D272A (SEQ ID NO: 19)

Underlining shows the alanine substitution codon and the bold text indicates the initiator methione. The downstream PCR primer used was 5'-AAG GCG GGG <u>GGA TCC</u> TAG CAG TGG CCG GAG GAG GCG AGC-3' (SEQ ID NO: 20)

Underlining corresponds to the BamHI restriction site and bold text indicates the stop codon. The DNA was sequenced to ensure authenticity and transformed into the T7 expression host E. coli BL21(DE3)pLysS.

(c) Expression and Purification of NF-IL6 TCD Protein

E. coli were grown in 4 liter LB "superbroth" (32 g tryptone, 20 g yeast extract, 5 gm NaCl, q.s. to 1 L, pH 7.4) at 37° C. and recombinant protein induced by adding 1 mM isopropyl β-D-thiogalactose (IPTG, United States Biochemical) and culturing for 4 hours. The cell pellet from IPTG-induced cultures was disrupted using freeze-thaw lysis and purified to homogeneity by sequential cation exchange chromatography as previously described by Brasier and Kumar (1994). Purified peptides were monitored by Coomassie Brilliant Blue staining after separation by 20% SDS-polyacrylamide gel electrophoresis (PAGE) as described by Brasier and Kumar (1994). Concentrations of purified proteins were determined spectrophotometrically (based on the assumption that cysteine residues appear as half cystines) using the value $E_{280}$=1400 Mcm$^{-1}$ (TCD WT, V267A, D268A, K269A, H270A, S271A, D272A) and $E_{280}$=7090 Mcm$^{-1}$ (W-TCD).

(d) DNA-binding assays

Electrophoretic gel mobility shift assays were performed with the double-stranded APRE M6 oligonucleotide labeled with [α-$^{32}$P] dATP by a Klenow polymerase "fill-in" reaction. Twenty-thousand cpm of labeled APRE M6, constituting 10 fmoles of probe, were employed in a total volume of 20 μl as described by Brasier and Kumar (1994), and Brasier et al. (1990).

Fluorescence polarization was used to quantitate TCD:F-APRE M6 binding. DNA binding was determined in a Beacon™ fluorescence polarimeter (sensitivity of detection to 10 pM) using the indicated concentrations of homogeneous fraction of NF-IL6 TCD peptides in the presence of F-APRE M6 DNA probe. Fluorescence polarization was determined according to the relationship:

$$P = \frac{I_{11} - I_\perp}{I_{11} + I_\perp}$$

where $I_{11}$ is the intensity of light emission parallel to excitation light plane and $I \perp$ is the intensity of light perpendicular to the excitation light plane. Under the conditions of the assay, where viscosity and temperature are constant, polarization is an accurate measure of the correlation time, an indicator of the molecular volume of the F-APRE M6 complex. Heyduk and Lee (1990); LeTilly and Royer (1993).

Example 2

FLUORESCENCE POLARIZATION TO QUANTITATE TCD WT:F-APRE M6 BINDING

The inventors previously demonstrated that the NF-IL6 peptide (amino acids 266-345), corresponding to the smallest trypsin-resistant fragment within the DNA complex, binds to APRE DNA in sequence-specific fashion (Brasier and Kumar (1994)). The sequences and organization of the TCD WT domains are shown in FIG. 1. Using gel mobility shift assays, the TCD WT peptide was determined to have an indistinguishable Kd for binding (36 nM) as the full length NF-IL6 (24-345) protein (Brasier and Kumar, 1994). The recombinant protein produced was purified to homogeneity by sequential, ion-exchange chromatography as shown previously (Brasier and Kumar, 1994). FIG. 2 shows data acquired from a single representative fluorescence polarization titration. Serial two-fold dilutions of recombinant homogeneous TCD WT were incubated in 1 ml volumes containing 0.5 nM F-APRE M6 probe for 1 hour prior to determination of fluorescence polarization. The polarization is a sigmoidal relationship with concentration of the TCD WT peptide. The sigmoidal curve was fitted to several models of DNA-binding; the simplest model that fit the data best was of a single-site bimolecular reaction expressed as:

TCD WT+F-APRE M6⇌TCD WT:F-APRE M6    (Eq. 1)

Nonlinear least square regression analysis run on commercially available software (SigmaPlot) was used to fit the raw data to the relationship:

$f(x)=(AX+BC)/(X+C)$ using the Levenberg-Marquart algorithm, where A is the maximum polarization, B the minimum and C the equilibrium disassociation constant (Kd, nM). In this particular curve, values of A=221 mP, B=52 mP and C=7.9 nM were obtained. In this single curve, over the TCD concentration that determines the Kd value, the mean residuals closely approximate zero, allowing an estimation of Kd (although at very low and high TCD concentrations, the residuals deviate from zero, probably due to peptide aggregation).

As a validation of the interpretation of the binding curve, the binding titration was reduced into its component "bound" and "free" component fractions for binding cooperativity analysis and determination of the presence of multiple binding sites by the method of Hill (FIG. 1, top right). The linear relationship, defined by least squares regression analysis, is described by:

Log (Bound/Free)=0.59+0.9 Log (Free) ($R^2$=0.99)

This result indicates that the term n, the number of binding sites, closely approximates unity, and the y-intercept-Log (Kd) estimates the Kd to be 3.9 nM, in good agreement with the curve-fitting algorithm. Finally, analysis of binding by the method of Scatchard (1949) also demonstrates a linear relationship relating Bound/Free=0.069–0.015(Bound) ($R^2$= 0.97). The Kd by this estimation is 6.7 nM, also in close agreement with the previous two estimates. These analyses are interpreted as indicating that the binding model (Eq. 1) and the extrapolation of the Kd value are valid representations of the TCD WT:F-APRE M6 interaction.

Example 3

EFFECT OF INDIVIDUAL ALANINE SUBSTITUTIONS IN THE CSSD ON COMPLEX FORMATION

A series of studies was undertaken to compare the effects of sequential alanine substitutions in the CSSD on the energetics of DNA-complex formation. The tested mutants are shown in FIG. 3. These peptides were expressed individually and purified to homogeneity. All of these peptides had indistinguishable binding specificity as determined by gel mobility shift assays. Analysis of the peptides TCD D268A, TCD K269A and TCD D272A showed that all had significantly different DNA-binding properties when compared to TCD WT in the fluorescence polarization assay. Table 3 compares binding properties with those of simultaneously determined values of the TCD WT (for n=4 studies) as a function of NaCl concentration at pH 7.5. The peptides TCD D268A and TCD D272A both bind F:APRE M6 more avidly than TCD WT, indicating the influence of charged interactions with DNA in the CSSD.

Example 4

EFFECTS OF NaCl ON THE THERMODYNAMICS OF TCD WT:F-APRE M6 BINDING

Figure 4A:
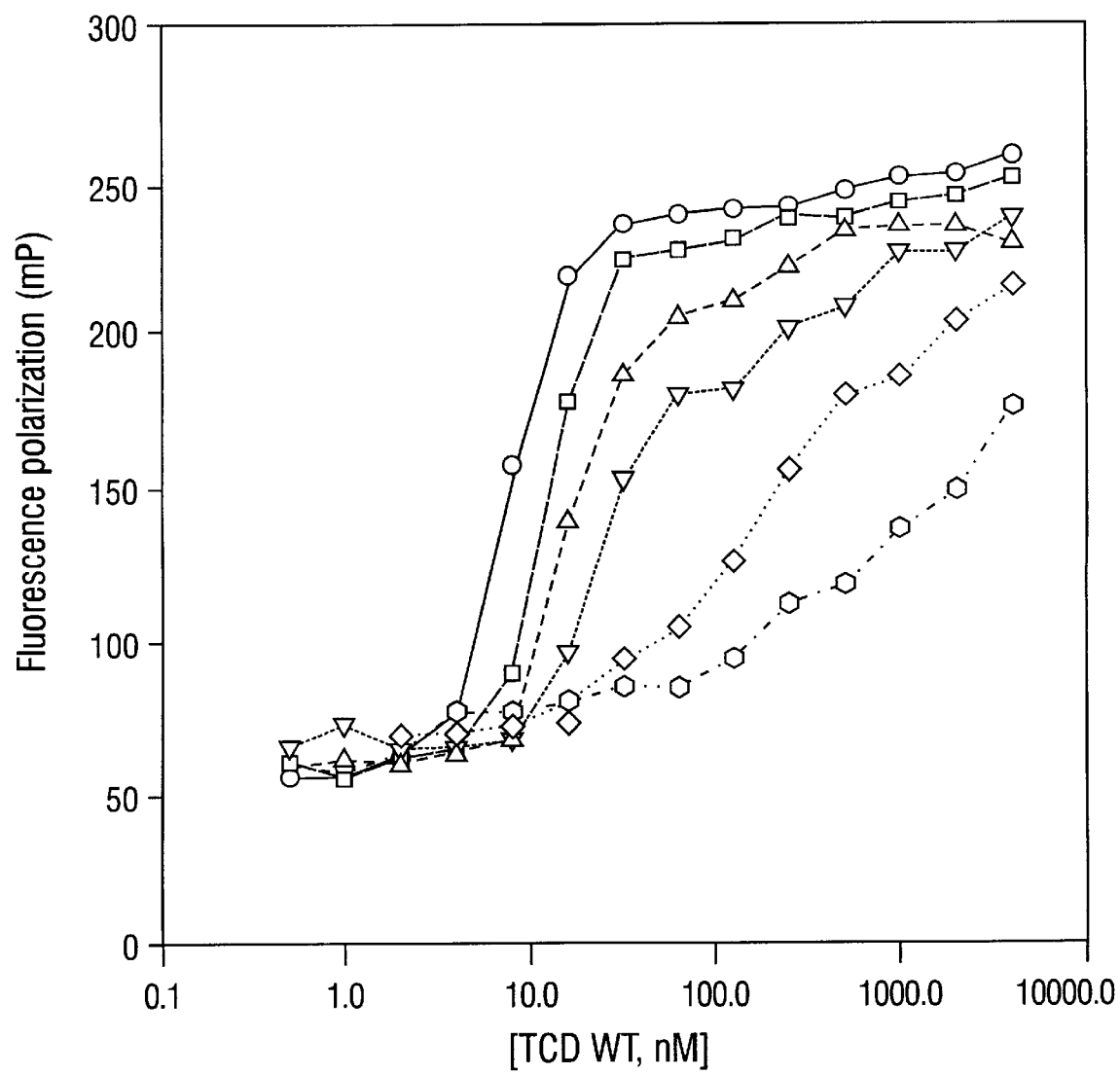
FIG. 4A—DEPENDENCE OF TCD WT BINDING TO F-APRE M6 AS A FUNCTION OF NaCl CONCENTRATION. Fluorescence polarization titrations using 0.5 nM F-APRE M6 in 1 ml of binding buffer (10 mM Tris-Cl, pH 7.5, 0.1 mM DTT) at 23° C. in the presence of increasing concentrations of NaCl. Each curve represents raw data from a serial dilution of TCD at the following NaCl concentrations: (●) 16 mM, (■) 25 mM, (▲) 40 mM, (▼) 63 mM, and (octagon) 158 mM NaCl. The presence of NaCl dramatically shifts the binding curve to the right.

Analysis of the effect of increasing concentrations of NaCl (16–158 mM) on TCD WT:APRE M6 complex formation is shown in FIG. 4A. The addition of NaCl markedly influences the affinity of TCD WT DNA-binding as evidenced by a rightward shift in the sigmoidal fluorescence polarization curves with increasing NaCl concentrations. Table 4 presents the calculated free energy of binding for the TCD WT:F-APRE M6 complex as a function of NaCl concentration. From these calculations, $\Delta G°_{obs}$ falls greater than 250-fold from –7.6 kcal/mol to –0.03 kcal/mol over a 10-fold increase in NaCl concentration.

Figure 4B:
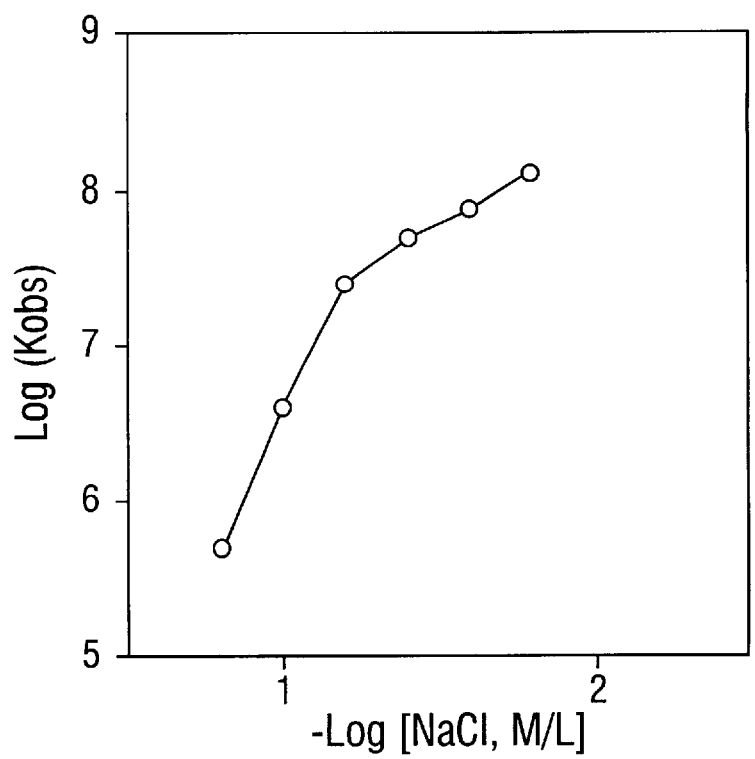
FIG. 4B—LOG-LOG PLOT OF DEPENDENCE OF $K_{obs}$ ON NaCl CONCENTRATION. Binding isotherms from the study shown in 4A were deconvoluted to determine the $K_{obs}$ for each salt concentration.
Figures 1, 4B:
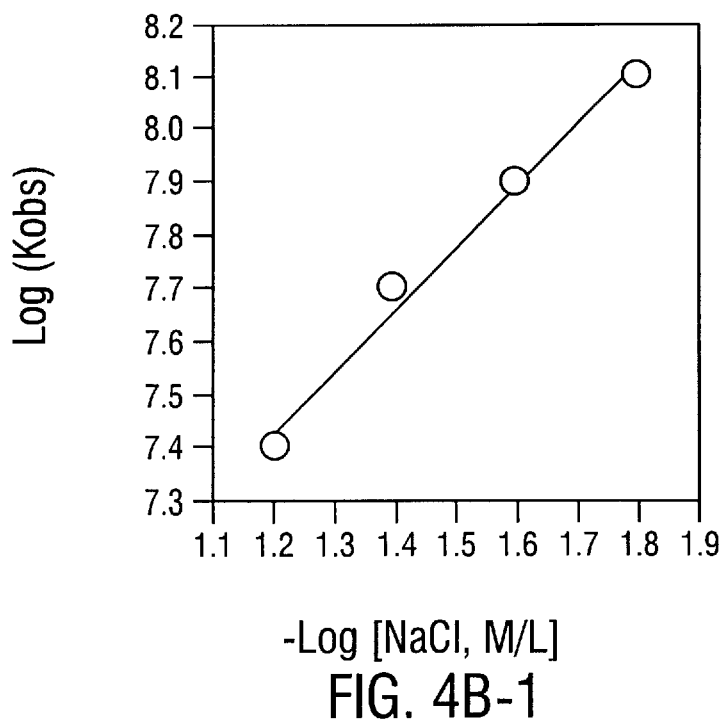
FIG. 1—Sequence and Domain Organization of the NF-IL-6 TCD Peptide. The NF-IL6 tryptic core domain spanning amino acids 266-345 is expressed in the T7 promoter/polymerase expression system. The peptide $NH^2$-terminus begins at $A^{266}$. The complex stabilizing subdomain (CSSD) represents the 6 $NH^2$-terminal amino acids from 266-272; the DNA-contact domain lies between 272-290 (Williams et al., 1991; Brasier and Kumar, 1994) and contains highly conserved amino acids with the GCN4 basic region demonstrated to make DNA contact (Ellenberger et al., 1992). The leucine zipper domain, beginning at V303, is responsible for orientation of the peptide as a parallel dimer stabilized by C-terminal disulfide bonds (C345) and interhelical salt bridges (Vinson, 1993; Krylov 1994).

To determine whether the NaCl effect on complex formation represents solely the contribution from entropic release of cation into the bulk solution, the dependence of Log($K_{obs}$) on Log[NaCl] was plotted (FIG. 4B). At low concentrations, 16–63 mM NaCl, the plot is a linear relationship. At concentrations above 63 mM NaCl, the Log ($K_{obs}$)-Log[NaCl] relationship for TCD WT:F-APRE M6 binding deviates significantly from a simple linear relationship. Between 63 and 158 mM NaCl, the relationship also is a linear function with a larger slope. This phenomenon is interpreted as indicating additional electrolyte interaction with species involved in TCD WT:F-APRE M6 complex formation (Record et al., 1976).

Example 5

EFFECT OF pH ON TCD WT:F-APRE M6 BINDING

Figure 5:
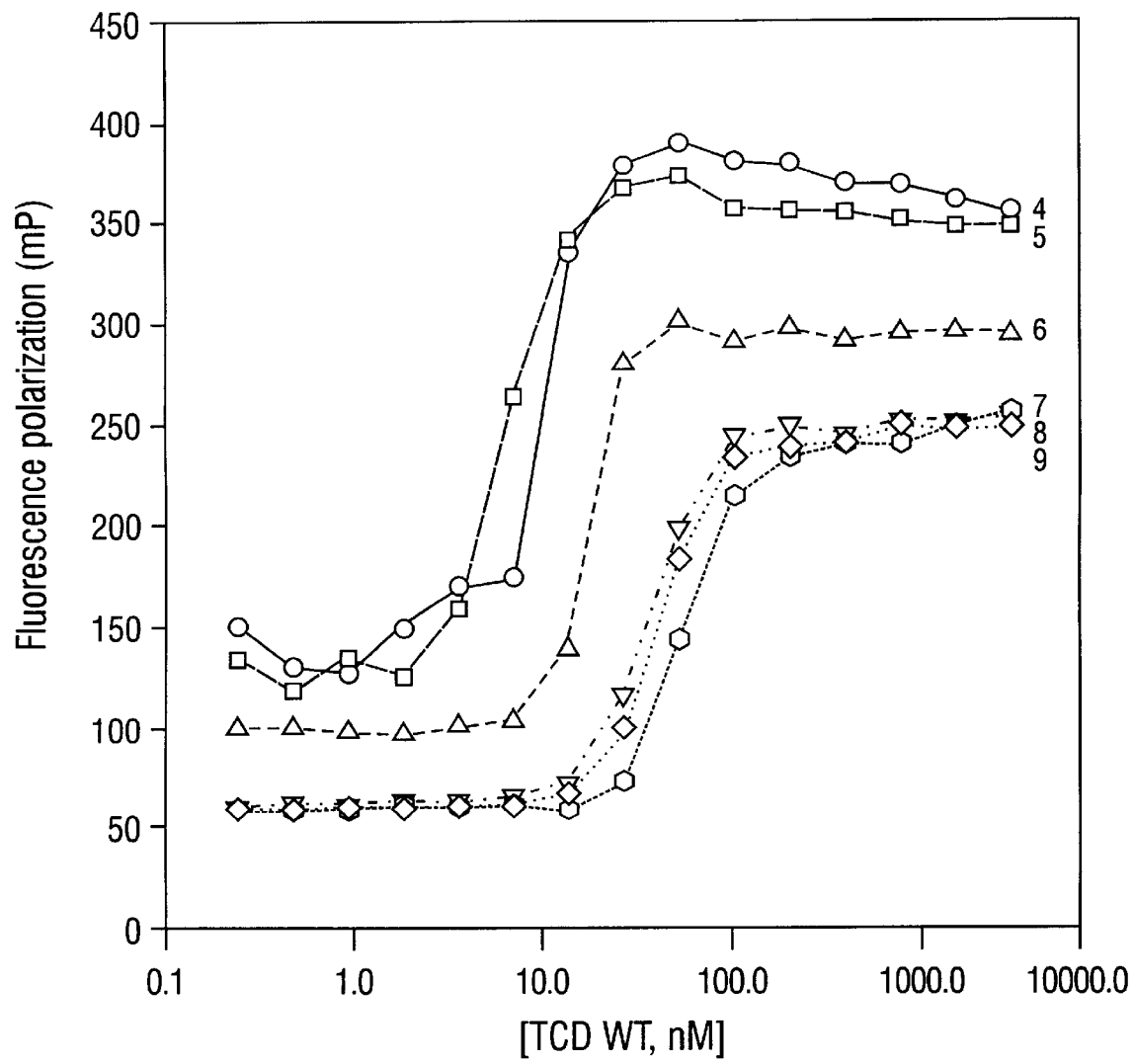
FIG. 5—DEPENDENCE OF TCD WT BINDING TO F-APRE M6 AS A FUNCTION OF pH. Fluorescence polarization titrations using recombinant TCD WT in 1 ml volume with 2 nM probe in 25 mM MES-25 mM HAc, 0.1 mM DTT 16 mM NaCl binding buffer between pH 4.0–9.0 (this buffer maintains a constant ionic strength independent of pH. Ellis and Morrison (1982). Each curve represents a titration of separately diluted TCD WT at different pH's according to the legend: (●) pH 4.0, (●) pH 5.0, (▲) pH 6.0, (▼) pH 7.0, and (octagon) pH 9.0. Each curve maintains a sigmoidal shape with similar differences in total polarization between free and bound APRE M6, although the acidic pH affects the absolute values for polarization. Free F-APRE M6 values (probe alone) were 150 mP (pH 4.0), 131 MP (pH 5.0), 96 mP (pH 6.0), 62 mP (pH 7.0), 58 mP (pH 8.0), 59 mP (pH 9.0). Note that the inflection of the sigmoidal curve shifts to the left between pH 7.0 to pH 4.0, indicating that TCD WT binds with higher affinity under acidic conditions.

In FIG. 5, the effect of pH on TCD WT:F-APRE M6 binding was determined in the presence of NaCl. At acidic pH's, binding affinity was increased as indicated by the leftward shift of the binding curves. In three independent studies, at pH 4.0 the $K_{obs}$ was $26\pm12\times10^7$ $M^{-1}L$; at pH 5.0, $K_{obs}$ was $36\pm15\times10^7$ $M^{-1}L$; at pH 6.0, $K_{obs}$ was $7.2\pm5\times10^7$ $M^{-1}L$; at pH 7.0, $K_{obs}$ was $3\pm3\times10^7$ $M^{-1}L$; at pH 8.0, $K_{obs}$ was $2.4\pm0.8\times10^7 M^{-1}L$; and at pH 9.0, $K_{obs}$ was $1.6\pm0.6\times10^7$ $M^{-1}L$. The calculated binding energetics in Table 5 indicate that the free energy of binding ($\Delta G°$) increases by $-1.2$ kcal/mol between pH 7.0 and pH 5.0. Moreover, the inventor notes that the term $\Delta Log$ $(K_{obs})/\Delta pH$ is discontinuous over the pH range 5.0–6.0, indicating the titration of side groups involved in the binding reaction.

Example 6

TITRATION OF NaCl EFFECTS ON TCD WT:F-APRE M6 BINDING

Figure 6A:
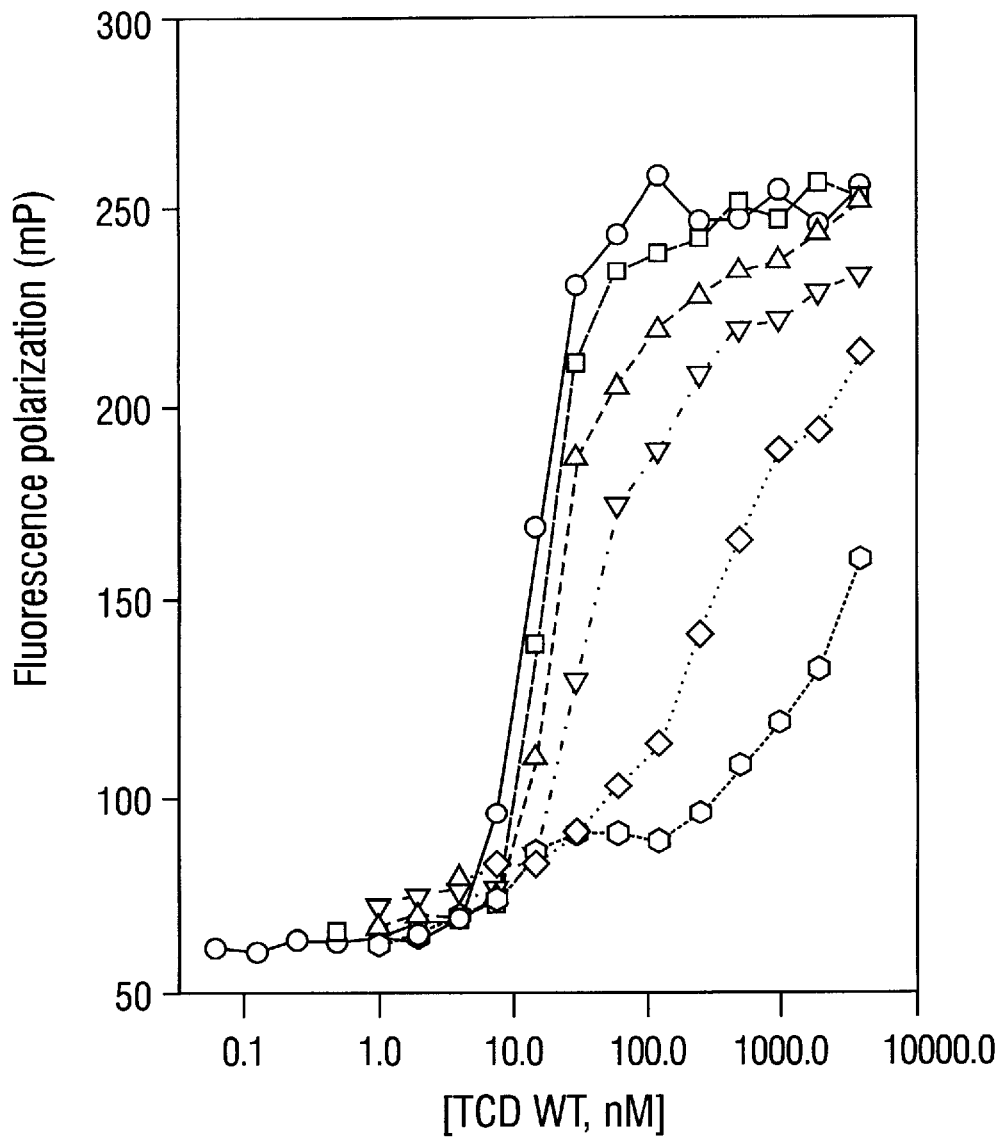
FIGS. 6A–6D—DEPENDENCE OF TCD WT BINDING TO F-APRE M6 ON NaCl CONCENTRATION AS A FUNCTION OF pH. Shown are three independent sets of binding isotherms for TCD WT binding F-APRE M6 versus NaCl concentrations from 16–158 mM at pH 5.0 (FIG. 6A), pH 6.0 (FIG. 6B) and pH 7.0 (FIG. 6C), for (●) 16 mM, (■) 25 mM, (▲) 40 mM, (▼) 63 mM, and (octagon) 158 mM, at 23° C. in isotonic buffer (25 mM MES-25 mM HAc, 0.1 mM DTT). TCD WT binding is markedly sensitive to NaCl at pH 7 and pH 6; however, at pH 5, the binding is NaCl-resistant.
Figure 6B:
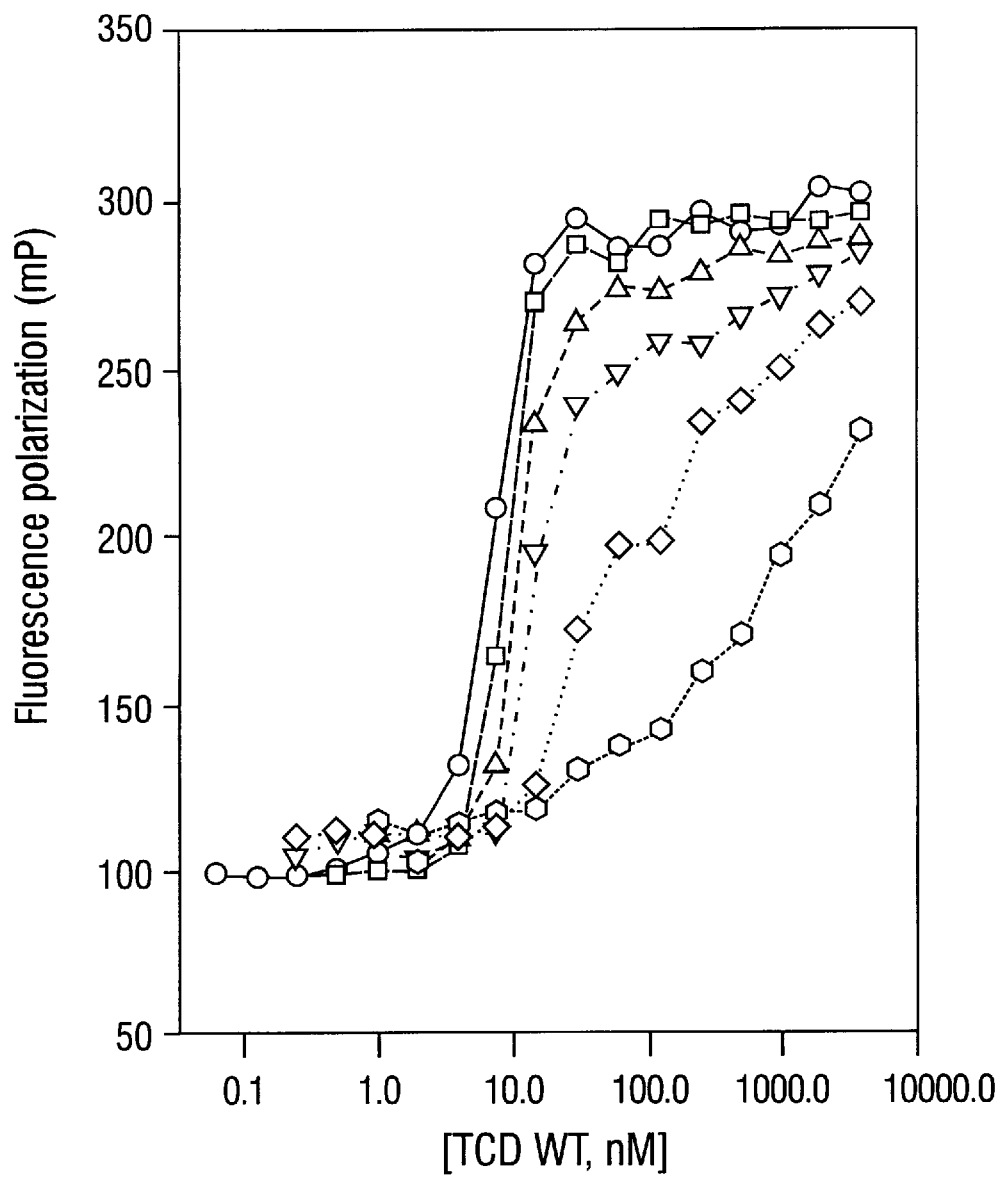
Figure 6C:
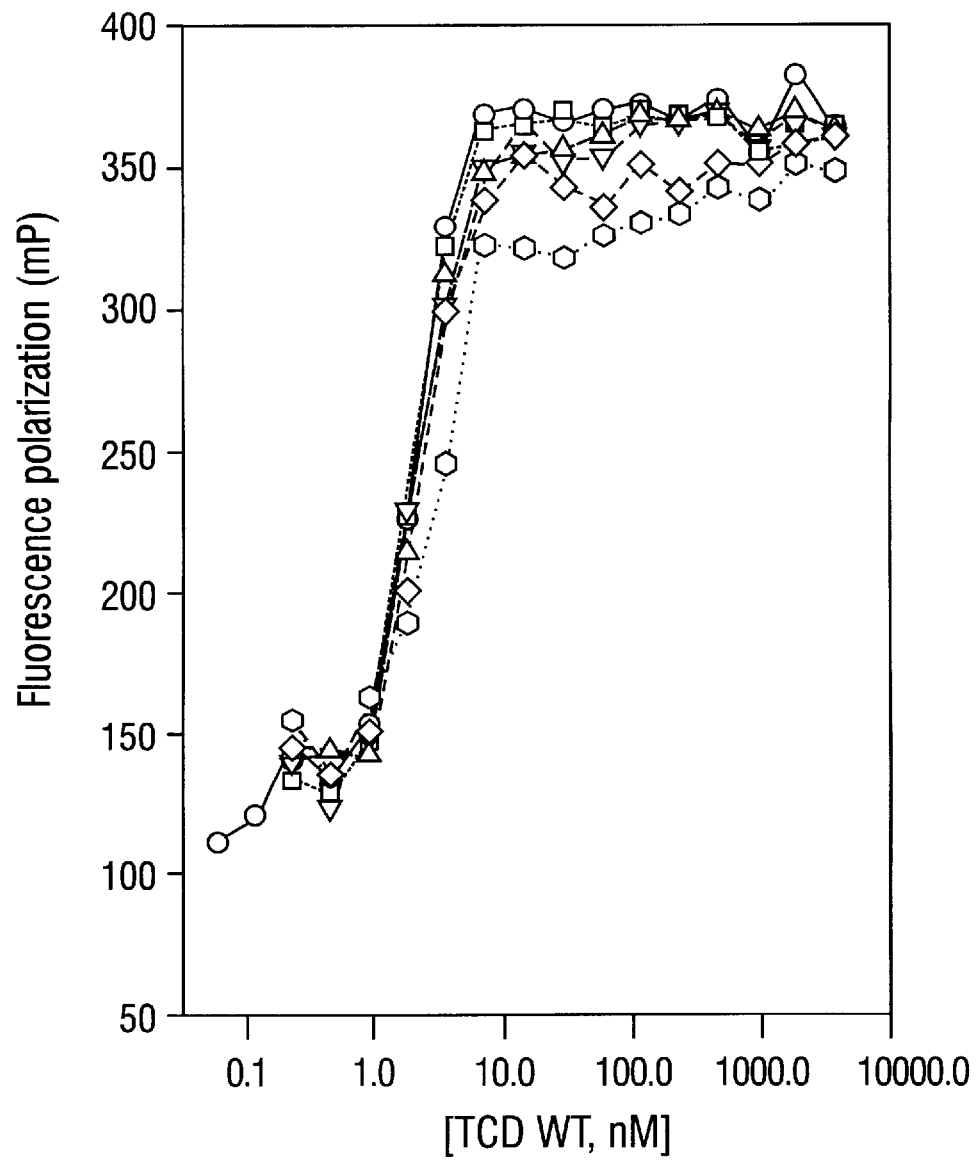
Figure 6D:
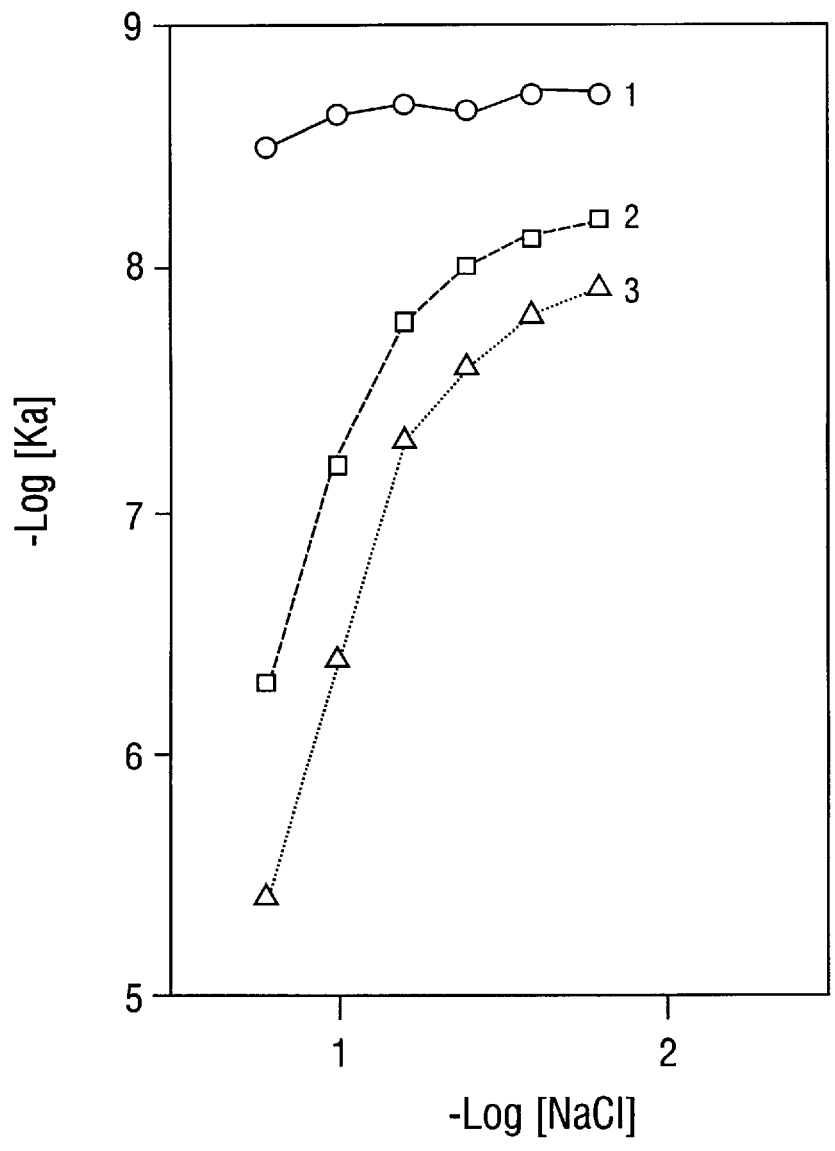

It was next determined whether the titratable TCD WT side groups were participating in the NaCl-sensitive interactions with F-APRE M6 by challenging the binding reactions with various NaCl concentrations over the pH range of 5.0–7.0 (FIG. 6A, FIG. 6B, FIG. 6C). At pH 6 and 7, the TCD WT:F-APRE M6 complex was sensitive to increasing submolar concentrations of NaCl (as described earlier for FIG. 3). In contrast, at pH 5.0, the TCD WT:F-APRE M6 complex was markedly less sensitive to NaCl. The Log $(K_{obs})$-Log[NaCl] plots for these isotherms are displayed in FIG. 6D. At both pH 7 and 6, a two-component function is seen; with an apparent inflection in the curve (at ~63 mM NaCl). In marked contrast, at pH 5, the relationship of Log($K_{obs}$) is a flattened linear function of Log[NaCl].

Example 7

EFFECT OF NaCl ON TCD D268A AND TCD D272A:F-APRE M6 BINDING

Figure 7C:
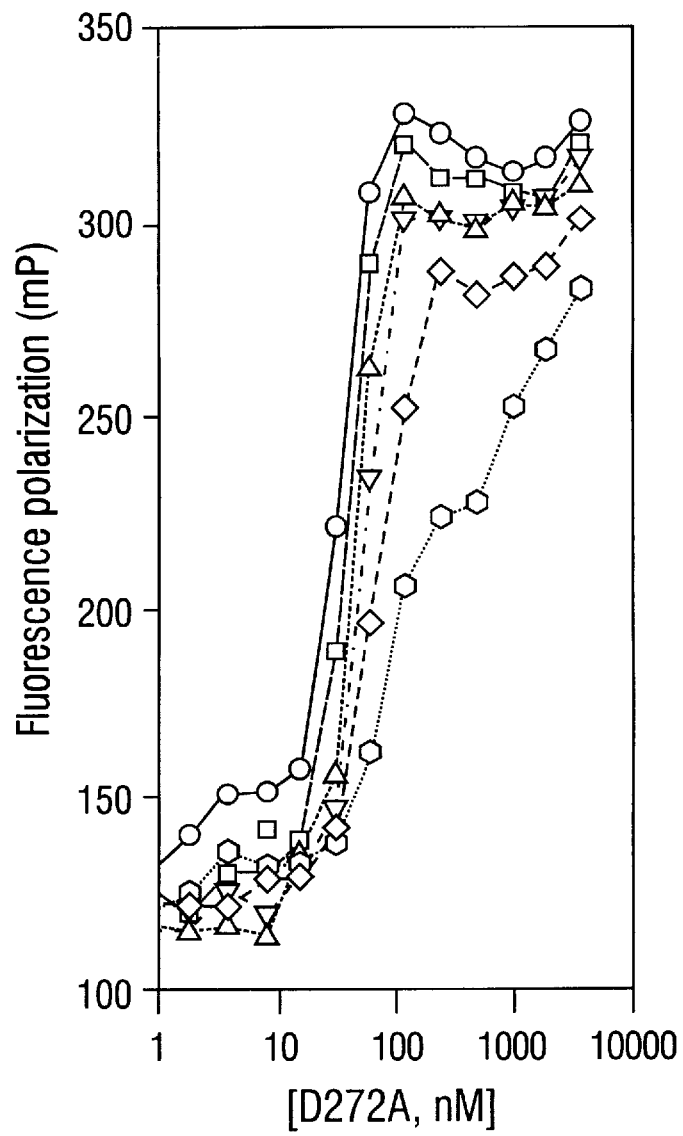

The dependence of TCD WT on NaCl and pH indicate the role for charged interactions with electrolyte in DNA complex formation. To examine the role of $Asp^{268}$ and $Asp^{272}$ in binding, a series of binding isotherms were assayed using these mutants and TCD WT with increasing NaCl concentrations (FIG. 7A, FIG. 7B, FIG. 7C). At every salt concentration, binding by D268A and D272A is higher affinity. Deconvolution of these binding isotherms into their respective $K_{obs}$ values and graphical representation as Log $(K_{obs})$ versus Log[NaCl] reveals that both TCD D268A and TCD D272A peptides have slightly flatter slopes than the respective TCD WT peptide.

Example 8

DISCUSSION OF RESULTS

Studies of TCD WT:F-APRE M6 complex formation in NaCl indicate involvement of additional electrolyte interactions, either binding or release, in controlling the DNA-binding energetics. At first glance, the basic amino acid-rich region of the NF-IL6 DNA contact domain would be expected to contribute multiple net ionic interactions with the DNA. Extrapolation of the Log $K_{obs}$-Log[NaCl] plot shown in FIG. 4A, at concentrations of NaCl where the $\Delta Log(K_{obs})/\Delta Log[NaCl]$ relationship is linear (16–63 mM NaCl), allows approximation of the net number of ion pairs formed as ~1. In other studies, the inventors have compared the effects of various sodium anions (fluoride, chloride, and acetate) and chloride cations (lithium, sodium, potassium, and cesium) on DNA-binding. Subtle differences in Log-Log plots can be observed for both systematic variation in counteranions, as well as cations, in DNA-binding. These data indicate the participation of both cations and anions in the binding reaction.

NF-IL6 binding of DNA is a discontinuous event between pH 7 and pH 4, with tighter binding at the lower pH. Even at pH 4, the strongly acidic DNA remains completely ionized, indicating that titratable side groups in the NF-IL6 peptide influence the DNA-binding reaction. The NF-IL6 bZIP peptide contains multiple titratable side groups with $pK_a$'s in the range of 4–7 (ignoring the contributions of the microenvironment). These include $H^{270}$ ($pK$~6.5), $D^{268,272,290}$ ($PK_a$~4.4) and nine glutamic acids ($pK_a$~4.4) throughout the basic region and leucine zipper. The present studies indicate the role of $D^{268}$ and $D^{272}$ as influencing DNA binding reactions through interactions with the electrolyte (we exclude the participation of $H^{270}$ in the pH shift because site-mutation of $H^{270}$ (TCD H270A) has wild type DNA-binding at neutral and acidic pH's). These mutations do not completely abolish the sensitivity of the peptides to salt or pH, however, and therefore other acidic side groups probably are involved in destabilizing the DNA complex at neutral pH.

Example 9

Materials and Methods (i) Identification of RSV-Induced Regulatory Mechanisms in IL-8 Induction Reverse transcriptase-polymerase chain reaction (RT-PCR) is used to measure changes in steady state IL-8 mRNA in response to RSV infection. Two $\mu$g of total cellular RNA is hybridized with oligo-dT and cDNA is synthesized using MMLV reverse transcriptase and dNTPs. cDNA is then used in the PCR reaction to amplify IL-8 cDNA using IL-8 gene specific primers. The abundance of IL-8 mRNA is then quantitated after agarose gel electrophoresis and ethidium bromide staining for nucleic acid. RSV infection increases IL-8 mRNA in a time-dependent fashion with a maximum induction between 12–24 hours. This is a reflection of increases in IL-8 transcription as measured by nuclear run-on analysis.

(ii) Overexpression and Purification of NF-IL6 DNA Tryptic Core Binding Domains (TCDs)

DNA encoding the 8.8 kDa region corresponding to the tryptic core domain is ligated into a T7 polymerase-based expression plasmid designated pET3d. In the bacterial host *E. coli* BL21(DE3)plysS, the addition of IPTG induces expression of the 79 amino acid peptide. In a large scale fermentation, 50 L of induced bacteria produce about 450 g of pellet, 10% of the total protein of which is TCD. Using this purification strategy, about 50 g of crude *E. coli* extract produces about 5 to about 8 milligrams of homogeneous NF-IL6 TCD, sufficient for peptide uptake studies.

(iii) Assays for Uptake of TCD by Cultured Cells

NF-IL6 TCD is covalently linked to fluorescein isothiocyanate (FITC) (Boehringer Mannheim) using a hydroxy succinimide ester linkage at a 5:1 molar ratio of FITC:TCD according to the suppliers recommendations, and desalted into sterile PBS for uptake studies. Cultured cells are incubated with labeled TCD for various periods of time (4–24 h), by adding FITC:TCD directly to the culture medium at concentrations of about 100 nM per peptide. At the time of harvest, cells were washed, fixed in acetone and visualized using Nikon fluorescence microscopy with standard excitation and emission wavelengths (100x).

If necessary, uptake of TCD by cultured cells may be improved by coupled to folate in order to take advantage of folate-receptor mediated endocytosis of intact proteins. Lee and Low (1994); Wang et al. (1995).

(iv) Effect of TCD on Cytokine Production by RSV

NF-IL6 TCD is encapsulated into pH-sensitive cholesterylhemisuccinate:phosphatidyl ethanolamine CHEMS:PE liposomes by the standard technique of sonicating the lipid:aqueous emulsion and extrusion through 0.45 μm membrane. Lai et al. (1985). Epithelial cells are treated with TCD-containing liposomes for 12 h prior to infection with sucrose gradient-purified RSV (Long strain 2) at a multiplicity of infection of 1. Epithelial cells are returned to culture and supernatants of the cell culture are removed for analysis of IL-8, IL-6 and G-CSF using commercially-available ELISAs. Time points for harvest are 12, 24, 36 and 48 h after exposure to RSV.

TABLE 3

| TCD Peptide | [NaCl] $mM.L^{-1}$ | Kobs ($\times 10^{-7}M^{-1}$.L) | $DG_{obs}$, kcal/mol |
|---|---|---|---|
| TCD WT | 50 | 11.8 | −10.8 |
| | 75 | 5.2 | −10.4 |
| | 100 | 1.3 | −9.6 |
| | 125 | 0.5 | −9.0 |
| TCD D268A | 50 | 13.6 | −11.0 |
| | 75 | 8.3 | −10.7 |
| | 100 | 2.8 | −10.0 |
| | 125 | 0.8 | −9.3 |
| TCD K269A | 50 | 6.8 | −10.6 |
| | 75 | 2.4 | −10.0 |
| | 100 | 0.5 | −9.0 |
| | 125 | 0.2 | −8.5 |
| TCD D272A | 50 | 8.8 | −10.7 |
| | 75 | 7.4 | −10.6 |
| | 100 | /3.3 | −10.1 |
| | 125 | 1.6 | −9.7 |

Table 3. Thermodynamics of CSSD alanine substitutions on F-APRE M6 complex formation as a function of NaCl. TCD peptides containing alanine substitutions at amino acids 268, 269, and 272 were analyzed for F-APRE M6 binding using fluorescence polarization in 1 ml of binding buffer containing 10 mM Tris HCl, pH 7.5 and 0.1 mM DTT and NaCl from 50 mM to 125 mM. $K_{obs}$ was determined and $\Delta G°_{obs}$ was calculated as described in Table 4.

TABLE 4

| [NaCl], $mM.L^{-4}$ | $K_{obs}$, $\times 10^{-7}M^{-1}$.L | $DG_{obs}$, kcal/mol |
|---|---|---|
| 16 | 12.9 | −10.9 |
| 25 | 7.9 | −10.6 |
| 40 | 5.1 | −10.3 |
| 63 | 2.5 | −9.9 |
| 100 | 0.39 | −8.9 |
| 158 | 0.05 | −7.6 |

Table 4. Thermodynamics of TCD WT:F-APRE M6 binding as a function of [NaCl]. Fluorescence polarization was measured to quantitate TCD WT:F-APRE M6 binding using 0.5 nM F-APRE M6 in a 1 ml volume using serial two-fold dilutions of TCD WT (taken from the data in FIG. 3) in the presence of 16–158 mM NaCl. Kobs, the observed equilibrium association constant defined as [TCD WT:F-APRE M6]/[TCD WT][F-APRE M6], was estimated using nonlinear curve fitting (Methods). $\Delta G°_{obs}$ was calculated using the relationship $\Delta G°_{obs}$=-RTLn (Kobs).

TABLE 5

| pH | [NaCl], $mM.L^{-1}$ | Kobs, $M^{-1}$.L | $\Delta G_{obs}$, Kcal/mol |
|---|---|---|---|
| 5 | 16 | 53.0 | −11.8 |
| | 25 | 52.0 | −11.8 |
| | 40 | 43.0 | −11.7 |
| | 63 | 48.0 | −11.7 |
| | 100 | 42.0 | −11.6 |
| | 158 | 29.0 | −11.4 |
| 6 | 16 | 15.0 | −11.0 |
| | 25 | 11.0 | −10.9 |
| | 40 | 8.3 | −10.7 |
| | 63 | 5.5 | −10.4 |
| | 100 | 1.5 | −9.7 |
| | 158 | 0.2 | −8.5 |
| 7 | 16 | 7.0 | −10.6 |
| | 25 | 5.2 | −10.4 |
| | 40 | 3.9 | −10.2 |
| | 63 | 2.0 | −9.9 |
| | 100 | 0.2 | −8.5 |
| | 158 | 0.02 | −7.1 |

Table 5. Thermodynamics of TCD WT:F-APRE M6 binding as a function of pH. Fluorescence polarization was measured to quantitate TCD WT:F-APRE M6 binding in the presence of NaCl concentrations from 16–158 mM at pH 5.0, 6.0, and 7.0 (taken from the data described in FIG. 5). $K_{obs}$ was determined and $\Delta G°_{obs}$ was calculated as described in Table 4.

I. REFERENCES

The following references, to the extent that they provide exemplary procedural or other details supplementary to those set forth herein, are specifically incorporated herein by reference:

Agre et al., "Cognate DNA binding specificity retained after leucine zipper exchange between GCN4 and C/EBP," *Science,* 246:922–926, 1989.

Akira et al., "A nuclear factor for IL-6 expression (NF-IL6) is a member of a C/EBP family," *EMBO J.,* 9:1897–1906, 1990.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Bangham et al., *J. Mol. Biol.,* 13:238–52 (1965).

Barkley et al., "Ion effects on the lac repressor-operator equilibrium," *Biochemistry,* 20:3842–3851, 1981.

Benvenisty and Neshif, "Direction introduction of genes into rats and expression of the genes," *Proc. Nat'l Acad. Sci. USA,* 83:9551–9555, 1986.

Blatter et al., "Identification of an amino acid-base contact in the GCN4-DNA complex by bromouracil-mediated photocrosslinking," *Nature,* 359:650–652, 1992.

Brasier et al., "A family of constitutive C/EBP-like DNA binding proteins attenuate the IL-1 alpha induced, NF kappa B mediated trans-activation of the angiotensinogen gene acute-phase response element," *EMBO J.,* 9:3933–3944, 1990.

Brasier et al., "Novel Expression of the Angiotensin Gene in a Pancreatic Islet Cell Line," transcriptional regulation by glucocorticoids, *J. Biol. Chem.,* 261:16148–54, 1986.

Brasier and Kumar, "Identification of a novel determinant for basic domain-leucine zipper (bZIP) DNA-binding activity in the acute-phase inducible nuclear factor-interleukin 6 transcription factor," *J. Biol. Chem.,* 269:10341–10351, 1994.

Cao et al., "Regulated expression of three C/EBP isoforms during adipose conversion of 3T3-L1 cells," *Genes Dev.,* 5:1538–1552, 1991.

Chang et al., "Molecular cloning of a transcription factor, AGP/EBP, that belongs to members of the c/ebp family," Mol. Cell Biol. 10:6642–6653, 1990.

Chen and Okayama, "High-efficiency transfection of mammalian cells by plasmid DNA," Mol. Cell Biol., 7:2745–2752, 1987.

Coffin, "Retroviridae and their replication," In: Virology, Fields et al. (eds.), New York: Raven Press, pp. 1437–1500, 1990.

Couch et al., "Immunization with types 4 and 7 adenovirus by selective infection of the intestinal tract," Am. Rev. Resp. Dis., 88:394–403, 1963.

Coupar et al., "A general method for the construction of recombinant vaccinia virus expressing multiple foreign genes," Gene, 68:1–10, 1988.

Cuenoud and Schepartz, "Design of a metallo-bZIP protein that discriminates between CRS and AP1 target sites: selection against AP1," Proc. Nat'l Acad. Sci. U.S.A., 90:1154–1159, 1993.

Curiel, "Gene transfer to respiratory epithelial cells via receptor mediated endocytosis," Am. J. Resp. Cell and Mol. Biol., 6:247, 1995.

Deamer and Uster, "Liposome Preparation: Methods and Mechanisms," LIPOSOMES, M. Ostro ed. (1983).

Descombes et al., "LAP, a novel member of the c/ebp gene family encodes a liver-enriched transcriptional activator protein," Genes & Development, 4:1541–1551, 1990.

Descombes and Schibler, "A liver-enriched transcriptional activator protein, LAP, and a transcriptional inhibitory protein, LIP, are translated from the same mRNA," Cell, 67:569–579, 1991.

Dubensky et al., "Direct transfection of viral and plasmid DNA into the liver or spleen of mice," Proc. Nat'l Acad. Sci. USA, 81:7529–7533, 1984.

Ellenberger et al., "The GCN4 basic region leucine zipper binds DNA as a dimer of uninterrupted alpha-helices: Crystal structure of the protein-DNA complex," Cell, 71:1223–1237, 1992.

Ellis and Morrison, "Buffers of constant ionic strength for studying pH-dependent processes," Meth. Enzym., 87:405, 1982.

Fechheimer et al., "Transfection of mammalian cells with plasmid DNA by scrape loading and sonication loading," Proc. Nat'l Acad. Sci. USA, 84:8463–8467, 1987.

Ferkol et al., FASEB J., 7:1081–1091, 1993.

Fraley et al., "Entrapment of a bacterial plasmid in phospholipid vesicles: Potential for gene transfer," Proc. Nat'l Acad. Sci. USA, 76:3348–3352, 1979.

Friedman et al., "Progress toward human gene therapy," Science, 244:1275–1281, 1989.

Friedman and McKnight, "Identification of two polypeptide segments of CCAAT/enhancer-binding protein required for transcriptional activation of the serum albumin gene," Genes Devel., 4:1416, 1990.

Ghosh-Choudhury, et al., "Protein IX, a minor component of the human adenovirus capsid, is essential for the packaging of full-length genomes," EMBO J., 6:1733–1739, 1987.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Glover and Harrison, "Crystal structure of the heterodimeric bZIP transcription factor c-Fos-c-Jun bound to DNA," Nature, 373:257–261, 1995.

Gomez-Foix et al., "Adenovirus-mediated transfer of the muscle glycogen phosphorylase gene into hepatocytes confers altered regulation of glycogen," J. Biol. Chem., 267:25129–25134, 1992.

Gopal, "Gene transfer method for transient gene expression, stable transfection, and cotransfection of suspension cell cultures," Mol. Cell Biol., 5:1188–1190, 1985.

Graham, et al., "Characteristics of a human cell line transformed by DNA from human adenovirus type 5", J. Gen. Virol., 36:59–72, 1977.

Graham and Prevec, "Manipulation of adenovirus vector," In: E. J. Murray (ed.), Methods in Molecular biology: Gene Transfer and Expression Protocol, Clifton, N.J.: Humana Press, 7:109–128, 1991.

Graham and Prevec, "Manipulation of adenovirus vectors," In E. J. Murray (ed.) Methods in Molecular Biology, Vol. 7: Gene transfer and expression protocols. Clifton, N. J.: The Humana Press, 1991.

Graham and van der Eb, "A new technique for the assay of infectivity of human adenovirus 5 DNA", Virology, 52:456–467, 1973.

Gregoriadis, DRUG CARRIERS IN BIOLOGY AND MEDICINE, G. Gregoriadis ed. (1979) pp. 287–341.

Grunhaus and Horwitz, "Adenovirus as cloning vector," Seminar in Virology, 3:237–252, 1992.

Harbury et al., "A switch between two-, three-, and four-stranded coiled coils in GCN4 leucine zipper mutants," Science, 262:1401–1407, 1993.

Harland and Weintraub, "Translation of mammalian mRNA injected into Zenopus oocytes is specifically inhibited by antisense RNA," J. Cell Biol., 101:1094–1099, 1985.

Hermonat and Muzycska, "Use of adenoassociated virus as a mammalian DNA cloning vector: Transduction of neomycin resistance into mammalian tissue culture cells," Proc. Nat'l Acad. Sci. USA, 81:6466–6470, 1984.

Hersdorffer et al., "Efficient gene transfer in live mice using a unique retroviral packaging line," DNA Cell Biol., 9:713–723, 1990.

Herz and Gerard, "Adenovirus-mediated transfer of low density lipoprotein receptor gene acutely accelerates cholesterol clearance in normal mice," Proc. Nat'l Acad. Sci. USA, 90:2812–2816, 1993.

Heyduk and Lee, "Application of fluorescence energy transfer and polarization to monitor Escherichia coli cAMP receptor protein and lac promoter interaction," Proc. Nat'l Acad. Sci. U.S.A., 87:1744–1748, 1990.

Horwich et al., "Synthesis of hepadenovirus particles that contain replication-defective duck hepatitis B Virus genomes in cultured HuH7 cells," J. Virol., 64:642–650, 1990.

Johnson, "Identification of C/EBP basic region residues involved in DNA sequence recognition and half-site spacing preference," Mol. Cell Biol., 13:6919–6930, 1993.

Johnson and McKnight, "Eukaryotic Transcriptional Regulatory Proteins," Ann. Rev. Biochem., 58:799–839, 1989.

Jones and Shenk, "Isolation of deletion and substitution mutants of adenovirus type 5," Cell, 13:181–188, 1978.

Kaneda et al., "Increased expression of DNA cointroduced with nuclear protein in adult rat liver," Science, 243:375–378, 1989.

Karlsson et al., EMBO J., 5:2377–2385, 1986.

Kato et al., "Expression of hepatitis B virus surface antigen in adult rat liver," J. Biol. Chem., 266:3361–3364, 1991.

Klein et al., "High-velocity microprojectiles for delivering nucleic acids into living cells," Nature, 327:70–73, 1987.

Kouzarides and Ziff, "The role of the leucine zipper in the fos-jun interaction," Nature, 336:646–651, 1988.

Krylov et al., "A thermodynamic scale for leucine zipper stability and dimerization specificity: e and g interhelical interactions," EMBO J., 13:2849–2861, 1994.

Lai et al., "Acid and calcium-induced structural changes in phosphatidylethanolamine membranes stabilized by cholesterol hemisuccinate," *Biochemistry,* 24:1654, 1985.

Landschulz et al., "The leucine zipper: A hypothetical structure common to a new class of DNA-binding proteins," *Science,* 240:1759, 1988.

Landschulz et al., "The DNA binding domain of the rat liver nuclear protein C/EBP is bipartite," *Science,* 243:1681–1688, 1989.

Le Gal La Salle et al., "An adenovirus vector for gene transfer into neurons and glia in the brain," *Science,* 259:988–990, 1993.

Lee and Low, "Delivery of liposomes into cultured KB cells via folate receptor mediated endocytosis," *J. Biol. Chem.,* 269:3198–3204, 1994.

Leirmo et al., "Replacement of potassium chloride by potassium glutamate dramatically enhances protein-DNA interactions in vitro," *Biochemistry,* 26:2095–2101, 1987.

Lenardo and Baltimore, "NF-kappa B: a pleiotropic mediator of inducible and tissue-specific gene control," *Cell,* 58:227–229, 1989.

LeTilly and Royer, "Fluorescence Anisotropy Assays Implicate Protein-Protein Interactions in Regulating trp Repressor DNA binding," *Biochemistry,* 32:7753–7758, 1993.

Levrero et al., "Defective and nondefective adenovirus vectors for expressing foreign genes in vitro and in vivo," *Gene,* 101:195–202, 1991.

Lohman and Mascotti, "Thermodynamics of ligand-nucleic acid interactions," *Meth. Enzymol.,* 212:400–424, 1992.

Mann et al., "Construction of a retrovirus packaging mutant and its use to produce helper-free defective retrovirus," *Cell,* 33:153–159, 1983.

Markowitz et al., "A safe packaging line for gene transfer: Separating viral genes on two different plasmids," *J. Virol.,* 62:1120–1124, 1988.

Mascotti and Lohman, "Thermodynamic extent of counterion release upon binding oligolysines to single-stranded nucleic acids," *Proc. Nat'l Acad. Sci. U.S.A.,* 87:3142–3146, 1990.

Mulligan, "The basic science of gene therapy," *Science,* 260:9260–932, 1993.

Myers, EPO 0273085.

Nicolas and Rubenstein, "Retroviral vectors," In: *Vectors: A survey of molecular cloning vectors and their uses,* Rodriguez & Denhardt (eds.), Stoneham: Butterworth, pp. 493–513, 1988.

Nicolau et al., "Liposomes as carriers for in vivo gene transfer and expression," *Methods Enzymol.,* 149:157–176, 1987.

Nicolau and Sene, "Liposome-mediated DNA transfer in eukaryotic cells," *Biochem. Biophys. Acta,* 721:185–190, 1982.

O'Neil et al., "DNA-induced increase in the alpha-helical content of C/EBP and GCN4," *Biochemistry,* 30:9030–9034, 1991.

O'Shea et al., "X-ray structure of the GCN4 leucine zipper, a two-stranded, parallel coiled coil," *Science,* 254:539–544, 1991.

Overman et al., *Biochemistry,* 27:456, 1988.

Paskind et al., "Dependence of moloney murine leukemia virus production on cell growth," *Virology,* 67:242–248, 1975.

Perales et al., *Proc Nat'l. Acad. Sci. USA,* 91:4086–4090, 1994.

Poli et al., "IL-6DBP, a nuclear protein involved in interleukin-6 signal transduction, defines a new family of leucine zipper proteins related to C/EBP," *Cell,* 63:643–653, 1990.

Potter et al., "Enhancer-dependent expression of human k immunoglobulin genes introduced into mouse pre-B lymphocytes by electroporation," *Proc. Nat. Acad. Sci. USA,* 81:7161–7165, 1984.

Pu and Struhl, "The leucine zipper symmetrically positions the adjacent basic region for specific DNA binding," *Proc. Nat'l Acad. Sci. U.S.A.,* 88:6901–6905, 1991.

Ragot et al., "Efficient adenovirus-mediated transfer of a human minidystrophin gene to skeletal muscle of mdx mice," *Nature,* 361:647–650, 1993.

Record et al., "Ion effects on ligand-nucleic acid interactions," *J. Mol. Biol.,* 107:145, 1976.

Record et al., "Thermodynamic analysis of ion effects on the binding and conformational equilibria of proteins and nucleic acids: the roles of ion association or release, screening, and ion effects on water activity," *Quar. Review Biophysics,* 11:103–178, 1978.

Record et al., "Analysis of equilibrium and kinetic measurements to determine thermodynamic origins of stability and specificity and mechanism of formation of site-specific complexes between proteins and helical DNA," *Meth. Enzymol.,* 208:291–342, 1991.

Renan, "Cancer genes: Current status, future prospects and applications in radiotherapy/oncology," *Radiother. Oncol.,* 19:197–218, 1990.

Rich et al., "Development and analysis of recombinant adenoviruses for gene therapy of cystic fibrosis," *Hum. Gene Ther.,* 4:461–476, 1993.

Ridgeway, "Mammalian expression vectors," In: *Vectors: A survey of molecular cloning vectors and their uses,* Rodriguez & Denhardt (eds.), Stoneham: Butterworth, pp. 467–92, 1988.

Rippe et al., "DNA-mediated gene transfer into adult rat hepatocytes in primary culture," *Mol. Cell Biol.,* 10:689–695, 1990.

Ron et al., "An inducible 50-kilodalton NF kappa B-like protein and a constitutive protein both bind the acute-phase response element of the angiotensinogen gene," *Mol. Cell Biol.,* 10:1023–1032, 1990.

Rosenfeld et al., "In vivo transfer of the human cystic fibrosis transmembrane conductance regulator gene to the airway epithelium," *Cell,* 68:143–155, 1992.

Ross, "Surfactant protein A-polylysine conjugates for delivery of DNA to airway cells in culture," *Human Gene Therapy,* 6:31–40, 1995.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079–9083, 1989.

Scatchard, "The attractions of proteins for small molecules and ions," *Ann. New York Acad. Sci.,* 51:660–672, 1949.

Shuman et al., "Evidence of changes in protease sensitivity and subunit exchange rate on DNA binding by C/EBP," *Science,* 249:771–774, 1990.

Stratford-Perricaudet et al., "Evaluation of the transfer and expression in mice of an enzyme-encoding gene using a human adenovirus vector," *Hum. Gene Ther.,* 1:241–256, 1990.

Stratford-Perricaudet and Perricaudet, "Gene transfer into animals: the promise of adenovirus," p. 51–61, In: *Human*

Gene Transfer, Eds, O. Cohen-Haguenauer and M. Boiron, Editions John Libbey Eurotext, France, 1991.

Studier et al., "Use of T7 RNA polymerase to direct expression of cloned genes," Meth. Enzmol., 185:60–89, 1990.

Szoka and Papahadjopoulos, Proc. Nat'l Acad. Sci. U.S.A., 75:4194–98, 1978.

Temin, "Retrovirus vectors for gene transfer: Efficient integration into and expression of exogenous DNA in vertebrate cell genome," In: Gene Transfer, Kucherlapati (ed.), New York: Plenum Press, pp. 149–188, 1986.

Tjian and Maniatis, "Transcriptional activation: A Complex puzzle with few easy pieces," Cell, 77:5–8, 1994.

Top et al., "Immunization with live types 7 and 4 adenovirus vaccines. II. Antibody response and protective effect against acute respiratory disease due to adenovirus type 7, " J. Infect. Dis., 134:155–160, 1971.

Tur-Kaspa et al., "Use of electroporation to introduce biologically active foreign genes into primary rat hepatocytes," Mol. Cell Biol., 6:716–718, 1986.

Varmus et al., "Retroviruses as mutagens: Insertion and excision of a nontransforming provirus alter the expression of a resident transforming provirus," Cell, 25:23–36, 1981.

Vinson et al., "Dimerization specificity of the leucine zipper-containing bZIP motif on DNA binding: prediction and rational design," Genes Devel., 7:1047–1058, 1993.

Wagner et al., Science, 260:1510–1513, 1990.

Wang et al., "Delivery of antisense oligodeoxyribonucleotides against the human EGF receptor into cultured KBV cells with liposomes conjugated to folate via polyethylene glycol," Proc. Nat'l Acad. Sci. U.S.A., 92:3318–3322, 1995.

Weiss et al., "Folding transition in the DNA-binding domain of GCN4 on specific binding to DNA 'see comments," Nature, 347:575–578, 1990.

Williams et al., "A family of c/ebp-related proteins capable of forming covalently linked leucine zipper dimers in vitro," Genes Devel., 5:1553–1567, 1991.

Wolffe, "Transcription: in tune with the histones," Cell, 77:13–16, 1994.

Wong et al., "Appearance of β-lactamase activity in animal cells upon liposome mediated gene transfer," Gene, 10:87–94, 1980.

Wu and Wu, "Receptor-mediated in vitro gene transfections by a soluble DNA carrier system," J. Biol. Chem., 262:4429–4432, 1987.

Wu and Wu, "Evidence for targeted gene delivery to HepG2 hepatoma cells in vitro," Biochemistry, 27:887–892, 1988.

Wu and Wu, Adv. Drug Delivery Rev., 12:159–167, 1993.

Yang et al., "In vivo and in vitro gene transfer to mammalian somatic cells by particle bombardment," Proc. Nat'l Acad. Sci. USA, 87:9568–8572, 1990.

Zelenin et al., "High-velocity mechanical DNA transfer of the chloramphenicol acetyltransferase gene into rodent liver, kidney and mammary gland cells in organ explants and in vivo," BS Lett., 280:94–96, 1991.

What is claimed is:

1. An isolated polypeptide comprising an NF-IL6 tryptic core domain, wherein the N-terminus of said core domain has a net charge that is less negative than the N-terminus of wild-type nuclear factor interleukin 6 (NF-IL6), and wherein the binding affinity of said polypeptide is higher than NF-IL6 for its target sequence.

2. The isolated polypeptide according to claim 1, wherein said tryptic core domain corresponds to residues 266 to 345 of wild-type NF-IL6 tryptic core domain.

3. The isolated polypeptide according to claim 1, wherein said N-terminus corresponds to residues 266 to 272 of wild-type NF-IL6 tryptic core domain.

4. The isolated polypeptide according to claim 3, wherein said N-terminus is at least one unit charge less negatively charged than wild-type NF-IL6 tryptic core domain.

5. The isolated polypeptide according to claim 3, wherein the N-terminus lacks one of the aspartic acid residues found in the wild-type NF-IL6 tryptic core domain and has substituted therefore an uncharged or positively charged residue.

6. The isolated polypeptide according to claim 3, wherein the N-terminus lacks both aspartic acid residues found in the wild-type NF-IL6 tryptic core domain and has substituted therefore at least one uncharged or positively charged residue.

7. The isolated polypeptide according to claim 5, wherein the substitution is an alanine, glycine or threonine residue.

8. The isolated polypeptide according to claim 5, wherein the substitution is an alanine residue.

9. The polypeptide according to claim 8, wherein the substitution is alanine for aspartic acid at position 268.

10. The polypeptide according to claim 8, wherein the substitution is alanine for aspartic acid at position 272.

11. The isolated polypeptide according to claim 6, wherein the substitution is alanine, glycine or threonine residues.

12. The isolated polypeptide according to claim 6, wherein the substitution is alanine residues.

13. The isolated polypeptide according to claim 6, wherein both aspartic acid residues are substituted with uncharged or positively charged residues.

14. The isolated polypeptide according to claim 13, wherein the substitutions are alanine, glycine or threonine residues.

15. The isolated polypeptide according to claim 13, wherein the substitutions are alanine residues.

16. A composition comprising:

(i) a polypeptide comprising an NF-IL6 tryptic core domain, wherein the N-terminus of said core domain has a net charge that is less negative that wild-type NF-IL6 tryptic core domain, and wherein the binding affinity of said polypeptide is higher than NF-IL6 for its target sequence; and (ii) a pharmaceutically acceptable carrier.

17. The composition according to claim 16, wherein said polypeptide is formulated with a liposome.

18. The composition according to claim 16, wherein said polypeptide is formulated with folate-conjugated bovine serum albumin.

19. A method for inhibiting NF-IL6 function in a cell in culture comprising the steps of:

(i) providing a polypeptide comprising an NF-IL6 tryptic core domain, wherein the N-terminus of said core domain has a net charge that is less negative than wild-type NF-IL6 tryptic core domain, and wherein the binding affinity of said polypeptide is higher than NF-IL6 for its target sequence; and (ii) contacting said cell with said polypeptide.

20. The method according to claim 19, wherein said polypeptide is formulated with a liposome.

21. The method according to claim 19, wherein said polypeptide is formulated with folate-conjugated bovine serum albumin.

* * * * *